(12) United States Patent
Hancu et al.

(10) Patent No.: US 7,303,741 B2
(45) Date of Patent: Dec. 4, 2007

(54) SYSTEMS AND METHODS FOR HIGH-RESOLUTION IN VIVO IMAGING OF BIOCHEMICAL ACTIVITY IN A LIVING ORGANISM

(75) Inventors: Ileana Hancu, Clifton Park, NY (US); Mohan Mark Amaratunga, Clifton Park, NY (US); Denyce Kramer Wicht, Saratoga Springs, NY (US); Paritosh Dhawale, Brookfield, WI (US); Nadeem Ishaque, Clifton Park, NY (US); Faisal Ahmed Syud, Guilderland, NY (US); Bruce Fletcher Johnson, Scotia, NY (US); Amy Casey Williams, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 801 days.

(21) Appl. No.: 10/252,311

(22) Filed: Sep. 23, 2002

(65) Prior Publication Data

US 2004/0057903 A1 Mar. 25, 2004

(51) Int. Cl.
*A61B 5/055* (2006.01)
(52) U.S. Cl. .................. 424/9.3; 424/9.36; 424/9.6
(58) Field of Classification Search .............. 424/9.3, 424/9.363, 9.365, 9.6; 436/172; 549/223; 600/420
See application file for complete search history.

(56) References Cited

U.S. PATENT DOCUMENTS

| | | | |
|---|---|---|---|
| 5,900,228 A | 5/1999 | Meade et al. | |
| 6,083,486 A | 7/2000 | Weissleder et al. | |
| 6,123,921 A | * 9/2000 | Meade et al. | ............. 424/9.363 |
| 6,217,848 B1 | 4/2001 | Achilefu et al. | |

FOREIGN PATENT DOCUMENTS

WO    WO 02/00265 A1    1/2002

OTHER PUBLICATIONS

Josephson et al. Bioconjugate Chem. 2002, 13, 554-560.*
Huber et al. Bioconjugate chem. 1998, 9, 242-249.*
Sanjay Tyagi et al., "Molecular Beacons: Probes that Fluoresce upon Hybridization", Nature Biotechnology, vol. 14, Mar. 1996, pp. 303-308, XP002926498.
International Search Report for International Application No. PCT/US03/25184, Date of Mailing: Feb. 9, 2004.
Bremer, Christoph et al., *Optical Imaging of Matrix Metalloproteinase-2 Activity in Tumors: Feasibility Study in a Mouse Model*, RADIOLOGY, Nov. 2001, pp. 523-529.
Bremer, Christoph et al., *In Vivo Molecular Target Assessment of Matrix Metalloproteinase Inhibition*, Nature Medicine, vol. 7, No. 6, Jun. 2001, pp. 743-748.
Tung, Ching-Hsuan et al., *In Vivo Imaging of Proteolytic Enzyme Activity Using a Novel Molecular Reporter*, Cancer Research, Sep. 1, 2000, pp. 4953-4958.
Mahmood, Umar et al., *Near-Infrared Optical Imaging of Protease Activity for Tumor Detection*, RADIOLOGY, Dec. 1999, pp. 866-870.
Tung, Ching-Hsuan et al., *Preparation of a Cathepsin D Sensitive Near-Infrared Fluorescence Probe for Imaging*, Bioconjugate Chem., vol. 10, No. 5, 1999, pp. 892-896.
Weissleder, Ralph et al., *In Vivo Imaging of Tumors with Protease-Activated Near-Infrared Fluorescent Probes*, Nature Biotechnology, vol. 17, Apr. 1999, pp. 375-378.
Achilefu, Samuel et al., *Novel Receptor-Targeted Fluorescent Contrast Agents for In vivo Tumor Imaging*, Investigative Radiology, vol. 35, Aug. 2000, pp. 479-485.
Huber, Martina M. et al., *Fluorescently Detectable Magnetic Resonance Imaging Agents*, Bioconjugate Chem., vol. 9, No. 2, 1998, pp. 242-249.
Becker, Andreas et al., *Receptor-Targeted Optical Imaging of Tumors with Near-Infrared Fluorescent Ligands*, Nature Biotechnology, vol. 19, Apr. 2001, pp. 327-331.
Licha, Kai et al., *Synthesis, Characterization, and Biological Properties of Cyanine-Labeled Somatostatin Analogues as Receptor-Targeted Fluorescent Probes*, Bioconjugate Chem., vol. 12, No. 1, 2001, pp. 44-50.
Becker, Andreas et al., *Cyanine Dye Labeled Vasoactive Intestinal Peptide and Somatostatin Analog for Optical Detection of Gastroenteropancreatic Tumors*, Annals of the New York Academy of Sciences, vol. 921, Dec. 2000, pp. 275-278.
Josephson, Lee et al., *Near-Infrared Fluorescent Nanoparticles as Combined MR/Optical Imaging Probes*, Bioconjugate Chem., vol. 13, No. 3, 2002, pp. 554-560.

* cited by examiner

Primary Examiner—Michael G. Hartley
Assistant Examiner—J Rogers
(74) Attorney, Agent, or Firm—Cantor Colburn LLP

(57) ABSTRACT

This invention relates to bifunctional detection agents useful for providing high-resolution, in vivo imaging of biochemical activity in a living organism. Methods of using these bifunctional detection agents may comprise administering them into a living organism, and then estimating the localization of the detection agent using one modality (i.e., MRI), while concurrently estimating the level of biological activity using a second modality (i.e., optical imaging). One of the bifunctional detection agents comprises a magnetic resonance component and an optical imaging component. The magnetic resonance component comprises a contrast agent that is always activated or "on". The optical imaging component comprises an activatable contrast agent or dye that is activated or turned "on" only in the presence of a particular event. For example, the optical imaging component may be activated by a certain wavelength of light and (1) by the presence of a particular biochemical marker, (2) by enzyme cleavage, or (3) by a change in the temperature or pH of the surrounding medium. These bifunctional detection agents allow both anatomical and functional/metabolic information to be obtained simultaneously.

3 Claims, 13 Drawing Sheets

SYSTEMS AND METHODS FOR HIGH-RESOLUTION IN VIVO IMAGING OF BIOCHEMICAL ACTIVITY IN A LIVING ORGANISM

FIELD OF THE INVENTION

The present invention relates generally to the field of medical diagnostic imaging. More particularly, the present invention relates to the design and synthesis of bifunctional contrast agents that are operable for both magnetic resonance imaging ("MRI") and optical imaging, and methods of using such agents to obtain high-resolution in vivo images of biochemical activity in a living organism.

BACKGROUND OF THE INVENTION

Magnetic resonance imaging ("MRI") was established over two decades ago as a medical diagnostic technique that offers high-resolution anatomical information about the human body, and has since been used for the detection of a multitude of diseases. MRI creates images of a body using the principles of nuclear magnetic resonance. MRI can generate thin-section images of any part of the body from any angle and/or direction, in a relatively short period of time, and without surgical invasion. MRI can also create "maps" of biochemical compounds within any cross section of the body.

MRI is possible in the human body because the body is filled with small biological magnets—the most important, for MRI purposes, being the nucleus of the hydrogen atom, also know as a proton. Once a patient is placed into a MRI unit, their body is placed in a steady magnetic field that is more than 30,000 times stronger than the Earth's magnetic field. The MRI stimulates the body with radio waves to change the steady-state orientation of the protons, causing them to align with the magnetic field in one direction or the other. Then, the MRI stops the radio waves and "listens" to the body's electromagnetic transmissions at a selected frequency. The transmitted signal is used to construct images of the internal body using principles similar to those developed for computerized axial tomography scanners (CAT scanners). Since the nuclear magnetic relaxation times of tissues and tumors differ, abnormalities can be visualized on the MRI-constructed image.

Optical imaging continues to gain more acceptance as a diagnostic modality since it does not expose patients to ionizing radiation. Optical imaging is based on the detection of differences in the absorption, scattering and/or fluorescence of normal and tumor tissues. One type of optical imaging comprises near-infrared fluorescent ("NIRF") imaging. Generally, in NIRF imaging, filtered light or a laser with a defined bandwidth is used as a source of excitation light. The excitation light travels through the body and when it encounters a NIRF molecule or optical imaging agent, the excitation light is absorbed. The fluorescent molecule (i.e., the optical imaging agent) then emits detectable light that is spectrally distinguishable from the excitation light (i.e, they are lights of different wavelengths). Generally, light that is detectable via NIRF imaging has a wavelength of approximately 600-1200 nm. The optical imaging agent increases the target:background ratio by several orders of magnitude, thereby enabling better visibility and distinguishability of the target area. Optical imaging agents can be designed so that they only emit detectable light upon the presence of a particular event (i.e., in the presence of a predetermined enzyme). Optical imaging, such as NIRF imaging, shows significant promise for detecting functional or metabolic changes, such as the overproduction of certain proteins or enzymes, in a body. This is useful because the majority of diseases induce early functional or metabolic changes in the body before anatomical changes occur. The ability to detect these metabolic changes allows for early detection, diagnosis and treatment of a disease, thereby improving the patient's chance of recovery and/or of being cured.

A contrast agent is often used in conjunction with MRI and/or optical imaging to improve and/or enhance the images obtained of a person's body. A contrast agent is a chemical substance that is introduced into the body to change the contrast between two tissues. Generally, MRI contrast agents comprise magnetic probes that are designed to enhance a given image by affecting the proton relaxation rate of the water molecules in proximity to the MRI contrast agent. This selective change of the $T_1$ (Spin-Lattice Relaxation Time) and $T_2$ (Spin-Spin Relaxation Time) of the tissues in the vicinity of the MRI contrast agents changes the contrast of the tissues visible via MRI. Generally, optical contrast agents comprise dyes designed to emit light when excited with outside radiation. This emitted light is then detected by an optical imaging device.

Contrast agents are administered to a person, typically via intravenous injection into their circulatory system, so that abnormalities in a person's vasculature, extracellular space and/or intracellular space can be visualized. Some contrast agents may stay in the person's vasculature and highlight the vasculature. Other contrast agents may penetrate the vessel walls and highlight abnormalities in the extracellular space or intracellular space through different mechanisms, like, for example, binding to receptors. After a contrast agent is injected into a tissue, the concentration of the contrast agent first increases, and then starts to decrease as the contrast agent is eliminated from the tissue. In general, a contrast enhancement is obtained in this manner because one tissue has a higher affinity or vascularity than another tissue. For example, most tumors have a greater MRI contrast agent uptake than the surrounding tissues, due to the increased vascularity and/or vessel wall permeability of the tumor, causing a shorter $T_1$ and a larger signal change via MRI.

Typical MRI contrast agents belong to one of two classes: (1) complexes of a paramagnetic metal ion, such as gadolinium (Gd), or (2) coated iron nanoparticles. As free metal ions are toxic to the body, they are typically complexed with other molecules or ions to prevent them from complexing with molecules in the body, thereby lessening their toxicity. Some typical MRI contrast agents include, but are not limited to: Gd-EDTA, Gd-DTPA, Gd-DOTA, Gd-BOPTA, Gd-DOPTA, Gd-DTPA-BMA (gadodiamide), feruimoxsil, ferumoxide and ferumoxtran.

Another class of MRI contrast agents—called "smart" contrast agents—includes contrast agents that are activated by the physiology of the body or a property of a tumor, i.e, agents that are activated by pH, temperature and/or the presence of certain enzymes or ions. Some examples of MRI smart contrast agents include, but are not limited to, contrast agents that are sensitive to the calcium concentration in a body, or those that are sensitive to pH.

"Smart" optical contrast agents have recently been used in vivo to monitor enzyme activity in the human body. These smart contrast agents only produce contrast in the presence of specific proteases. Since proteases are key factors involved in multiple disease processes, the ability to tailor contrast agents or probes to specific enzymes should ultimately allow one to detect the expression levels of marker enzymes for various pathologic conditions. This approach is capable of providing all the necessary information for studying pathologies near the surface of the skin via optical imaging. However, since low localization information is characteristic of optical imaging, one or more additional modalities may be required for diagnosing pathologies deeper within the body.

Contrast agents are not only useful, but are often times required in order to make the presence of certain diseases detectable. For example, the mechanisms of contrast in MRI (such as $T_1$, $T_2$ and/or proton density) are somewhat limited, allowing certain diseases to remain undetectable by MRI in the absence of exogenous contrast agents. This is because none of the parameters that influence contrast are affected in some diseases without the addition of a contrast agent. Therefore, using contrast agents in conjunction with MRI offers excellent sensitivity for detecting some additional pathologic conditions, thereby allowing some diseases to be detected that would otherwise be undetectable via MRI alone. For example, MRI in the presence of contrast agents has very high sensitivity for detecting breast tumors, but very low specificity for the detection of cancerous tissue. The specificity for identifying cancerous tissue is so low via MRI because multiple pathologies, such as the recruitment and production of new blood vessels, are characterized by markers similar to those of cancerous tissue.

While both MRI and optical imaging provide useful information, neither independently provides all the information desired to help make early diagnoses of all diseases. As previously discussed, the majority of diseases induce early functional or metabolic changes in the body before anatomical changes occur. While these metabolic changes are almost impossible to detect via current MRI techniques, optical imaging shows significant promise in being able to detect such changes. However, when applications such as breast imaging are envisioned, optical imaging by itself is very limited by the spatial resolution that can be achieved. Roughly speaking, the spatial resolution of an optical image is about one-third of the distance between the source and the detector, which translates to about a 3 cm precision for localizing a small lesion in a 9 cm breast. This imprecision in localizing pathology via optical imaging might have proven to be an insurmountable drawback, leading an otherwise promising diagnostic technique to go unused. However, it is known to be advantageous to utilize MRI and optical imaging together to obtain more complete anatomical and functional information, thereby aiding in the early detection of disease. In fact, optical imaging and MRI are inherently compatible with one another, and concurrent MRI and optical images of breasts have already been acquired. However, no single bifunctional contrast agent comprising an always-activated magnetic resonance component for enhancing anatomical information and an activatable optical component for enhancing functional information currently exists.

Many contrast agents and/or detection agents are known. However, many are only unifunctional, not bifunctional. The prior art regarding unifunctional contrast agents does not suggest that it is possible to use a single detection agent to obtain images from two different modalities concurrently. While some bifunctional detection agents are known, none of them comprise an always-activated first component and an activatable second component that only emits detectable signals in the presence of a predetermined event (i.e., emits detectable light only in the presence of a particular enzyme). Furthermore, none of the prior art regarding bifunctional contrast agents discloses or suggests using an activatable optical imaging component, nor of combining a magnetic resonance imaging agent with an activatable optical imaging component.

Therefore, there is a need for systems and methods that can be used to further aid in the early detection of disease. There is also a need for systems and methods that allow for high-resolution localization of biochemical activity in a living organism. There is also a need for bifunctional contrast agents that can be utilized in two different modalities concurrently. There is yet a further need for bifunctional contrast agents that can be utilized in both MRI and optical imaging concurrently. There is still a further need for bifunctional contrast agents comprising an always-activated first component for obtaining enhanced anatomical information and an activatable second component for obtaining enhanced functional information. Finally, there is a need for bifunctional contrast agents wherein one component is an activatable component that is activatable only in the presence of a predetermined event.

SUMMARY OF THE INVENTION

Accordingly, the above-identified shortcomings of existing contrast agents and methods of using them are overcome by embodiments of the present invention. Embodiments of the present invention provide systems and methods that aid in the early detection of disease. These systems and methods allow for high-resolution in vivo imaging of the localization of biochemical activity in a living organism. Embodiments of the present invention may comprise bifunctional contrast agents that can be utilized in two different modalities concurrently. One embodiment comprises a bifunctional contrast agent that may be utilized in both MRI and optical imaging concurrently. Embodiments of these bifunctional contrast agents may comprise an always-activated first component for obtaining enhanced anatomical information and an activatable second component for obtaining enhanced functional information. In embodiments, these bifunctional contrast agents may comprise one activatable component that is activatable only in the presence of a predetermined event.

The present invention relates to bifunctional contrast agents or probes, and methods of using the same. One embodiment of the present invention comprises a bifunctional contrast agent or probe useful for both MRI and optical imaging simultaneously. In embodiments, these bifunctional contrast agents comprise a magnetic resonance component and an optical imaging component. In embodiments, the optical imaging component comprises one dye molecule and a quencher. In other embodiments, the optical imaging component comprises two dye molecules. In yet further embodiments, the optical imaging component comprises multiple dye molecules and multiple quenchers.

In accordance with the needs outlined above, embodiments of the present invention provide bifunctional detection agents, each comprising at least one activatable optical contrast agent or dye covalently linked to at least one magnetic resonance contrast agent. In one embodiment, the bifunctional detection agent comprises a magnetic resonance contrast agent covalently linked to both an optical dye and a quencher molecule, wherein the dye and quencher are linked such that when the bifunctional detection agent is excited with light of a certain wavelength, the quencher efficiently absorbs the emitted light so as to reduce the amount of light being detected by the optical detector. The magnetic resonance contrast agent may comprise a chelated gadolinium complex (i.e., Gd-DTPA or Gd-DOTA), a coated iron oxide nanoparticle, or the like. The linker can be designed so that close proximity of the dye and quencher molecule is achieved either through chemical bonds or through space. Furthermore, the linker may be designed such that, as the result of some biological or signaling process (i.e., enzyme cleavage), the proximity of the dye and the quencher is compromised (i.e., the distance between the dye and the quencher is increased), thereby allowing light to be emitted and detected by an optical imaging device.

One embodiment of the present invention provides bifunctional detection agents that are designed to allow simultaneous MRI and optical imaging of a target area so as to allow both anatomical and functional (i.e., metabolic) information to be obtained contemporaneously. The anatomical information is obtained via MRI and the magnetic resonance contrast agent, while the functional/metabolic information is obtained via optical imaging and the optical dye(s) and/or quencher. In embodiments of the present invention, the magnetic resonance contrast agent is designed so as to always be "on" (i.e., always be activated and/or detectable), while the optical contrast agent is designed so as to only be "on" when the dye is no longer in close proximity to the quenching molecule (i.e., the optical contrast agent is activatable so as to only be "on" or activated or detectable when light of a specific wavelength activates or excites the optical contrast agent and the presence of a particular enzyme causes cleavage between the dye and the quenching molecule). If one excites the contrast agent with light of the appropriate wavelength, the dye in the contrast agent will absorb the excitation light and re-emit radiation. As long as the dye and the quencher are in close proximity to one another, this re-emitted radiation/light will be absorbed by the quencher, so no significant fraction of the re-emitted light will hit the optical detector. In this case, the optical contrast agent is deemed to be "off." However, if the dye and the quencher move apart from one another (i.e., because of cleavage, bond breakage or conformation change), the dye will still absorb the excitation light, and will re-emit radiation of a slightly different wavelength. This re-emitted radiation/light will not be absorbed by the quencher because the dye and the quencher are too far apart, and therefore, the light will be detected by the optical detector. In this case, the optical contrast agent is deemed to be "on."

One aspect of the present invention relates to the co-localization of the bifunctional agent. This co-localization is possible because the magnetic resonance contrast agent and the optical contrast agent/dye are covalently bound together. Another aspect of embodiments of the present invention is that the magnetic resonance component and the optical component are also covalently bound to a quencher molecule that, due to its close proximity to the dye, efficiently absorbs the emitted light of the excited optical contrast agent. Yet another aspect of the present invention is that the magnetic resonance contrast agent and the optical dye remain covalently bound while a biological signaling process (i.e., enzyme cleavage) diminishes the close proximity of the quencher molecule, thereby activating the optical contrast agent and turning it "on". The optical signal produced by the activatable optical contrast agent is directly related to the biological signaling process, thereby allowing functional information to be detected.

The present invention has all the advantages associated with anatomical imaging using current magnetic resonance contrast agents, but also allows functional information to be obtained simultaneously via optical imaging. The bifunctional MRI/optical imaging contrast agents of the present invention make the simultaneous gathering of high-resolution anatomical and functional information possible. Preferably, the optical component of these contrast agents is only activated in the presence of a particular event (i.e., only when a particular enzyme is present in a person's body and light of a specific wavelength excites the optical contrast agent).

Embodiments of the present invention comprise a bifunctional detection agent comprising a magnetic resonance imaging component and an activatable optical imaging component, preferably, covalently linked to one another. In an embodiment, the magnetic resonance imaging component and the optical imaging component are contained in a single bifunctional detection agent. The bifunctional detection agents of the present invention allow magnetic resonance images and optical images of a living organism to be obtained, preferably concurrently. In an embodiment, the activatable optical imaging component is activated only in the presence of light of a predetermined wavelength and only in the presence of a predetermined event, such as in the presence of a predetermined enzyme, and/or when enzymatic cleavage occurs at fluorescence activation sites. In one embodiment, the magnetic resonance imaging component of the present invention may be continually activated and comprise a paramagnetic material such as a chelated gadolinium complex; a chelate of a paramagnetic ion such as europium (Eu), dysprosium (Dy), terbium (Tb), holmium (Ho), erbium (Er), thulium (Tm), or ytterbium (Yb); a coated iron nanoparticle; or the like. The activatable optical imaging component of the present invention comprises at least one optical dye, and may also comprise at least one quencher (which may also be a dye). The magnetic resonance imaging component of the present invention allows enhanced anatomical information to be obtained, while the activatable optical imaging component allows enhanced functional/metabolic information to be obtained. Herein, "enhanced" means that the image or information obtained by using the bifunctional contrast agent is of improved quality over the image or information that would be obtained by using no contrast agent.

Embodiments of the present invention comprise a bifunctional detection agent comprising a first component capable of enhancing anatomical information in a living organism and an activatable second component capable of enhancing functional/metabolic information in a living organism. In an embodiment of the present invention, the first component and the second component are contained in a single bifunctional detection agent. In embodiments, the enhanced anatomical information and the enhanced functional information are obtained simultaneously. In an embodiment, the first component is always activated or "on", while the activatable second component is activated or turned "on" only in the presence of a predetermined event, such as in the presence of light of a predetermined wavelength and (1) in the presence of a predetermined enzyme, (2) when enzymatic cleavage occurs at fluorescence activation sites, (3) when the temperature exceeds or falls below a predetermined value, or (4) when the pH exceeds or falls below a predetermined value. The enhanced anatomical information may be obtained via computed tomography, positron emission tomography, or magnetic resonance imaging. The enhanced functional information may be obtained via near-infrared fluorescence imaging.

Embodiments of the present invention also comprise a method of obtaining high-resolution, in vivo imaging of biochemical activity in a body, comprising the steps of administering a bifunctional detection agent of the present invention to a living organism; obtaining an image of anatomical information of the living organism; and obtaining an image of functional/metabolic information of the living organism. These images may be obtained concurrently. In an embodiment, the bifunctional detection agent is administered intravenously, but it may also be administered in any other suitable manner such as orally or intramuscularly. In embodiments, the image of anatomical information may be obtained via computed tomography, positron emission tomography, or magnetic resonance imaging. In embodiments, the image of functional information may be obtained via optical imaging.

Embodiments of the present invention also comprise systems for obtaining high-resolution, in vivo imaging of biochemical activity in a body. One system comprises a first imaging device capable of detecting a first imaging component of a bifunctional detection agent to obtain images of anatomical information of the living organism and a second imaging device capable of detecting an activatable second imaging component of the bifunctional detection agent to obtain images of functional/metabolic information of the living organism. The first imaging device and the second imaging device may be capable of being utilized simultaneously, and the activatable second imaging component of the bifunctional detection agent may be activated only in the presence of a predetermined event. The first imaging device may comprise a magnetic resonance imaging device, a computed tomography device, or a positron emission tomography device. The second imaging device may comprise an optical imaging device. In an embodiment, the first imaging device comprises a magnetic resonance imaging device and the second imaging device comprises an optical imaging device. In embodiments, the first imaging device and the second imaging device may be utilized simultaneously.

Further features, aspects and advantages of the present invention will be more readily apparent to those skilled in the art during the course of the following description, wherein references are made to the accompanying figures which illustrate some preferred forms of the present invention, and wherein like characters of reference designate like parts throughout the drawings.

DETAILED DESCRIPTION OF THE INVENTION

Figure 1A:
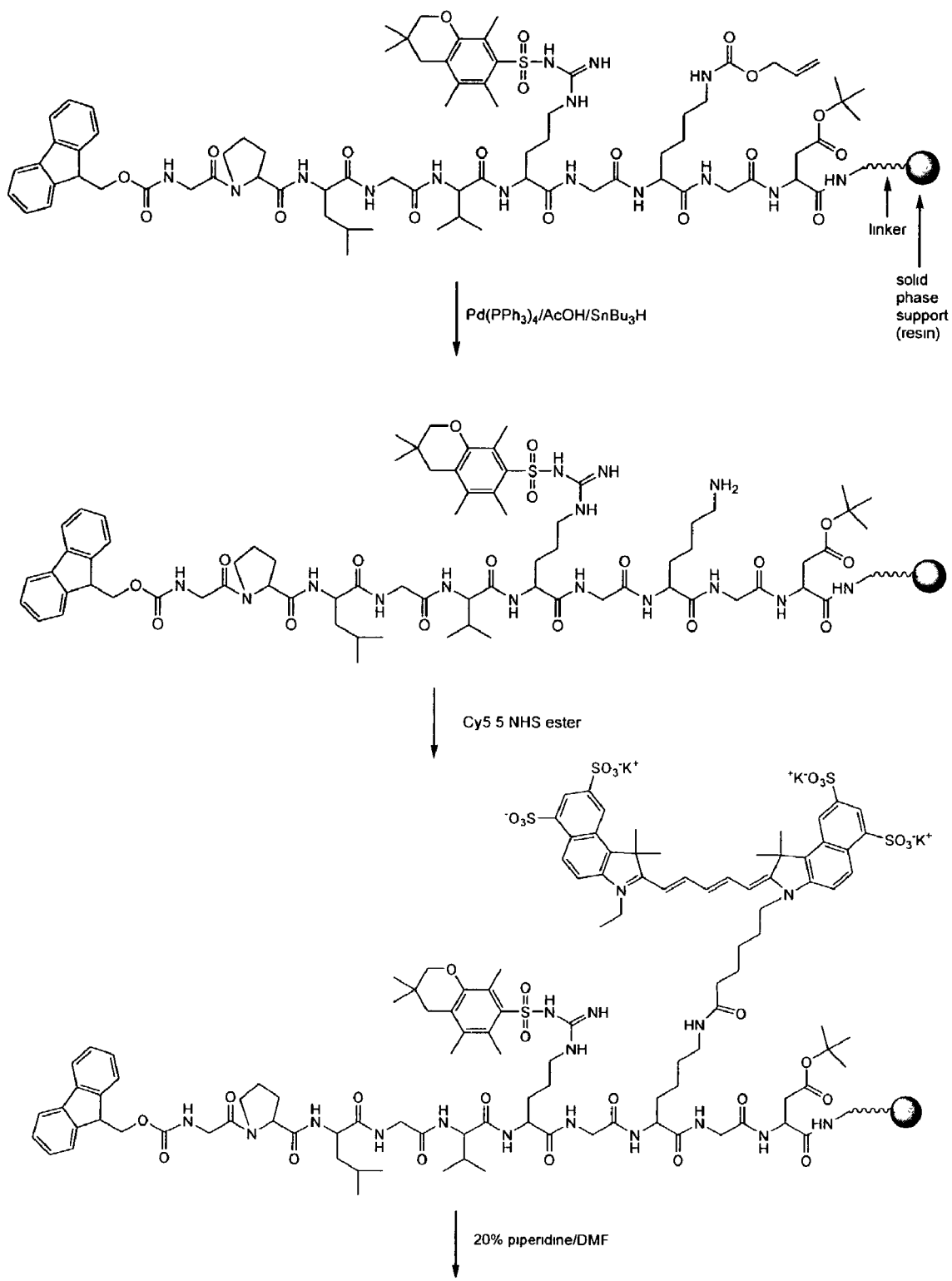
FIGS. 1A-1E show the synthesis of a bifunctional detection agent in accordance with one exemplary embodiment of the present invention.
Figure 1B:
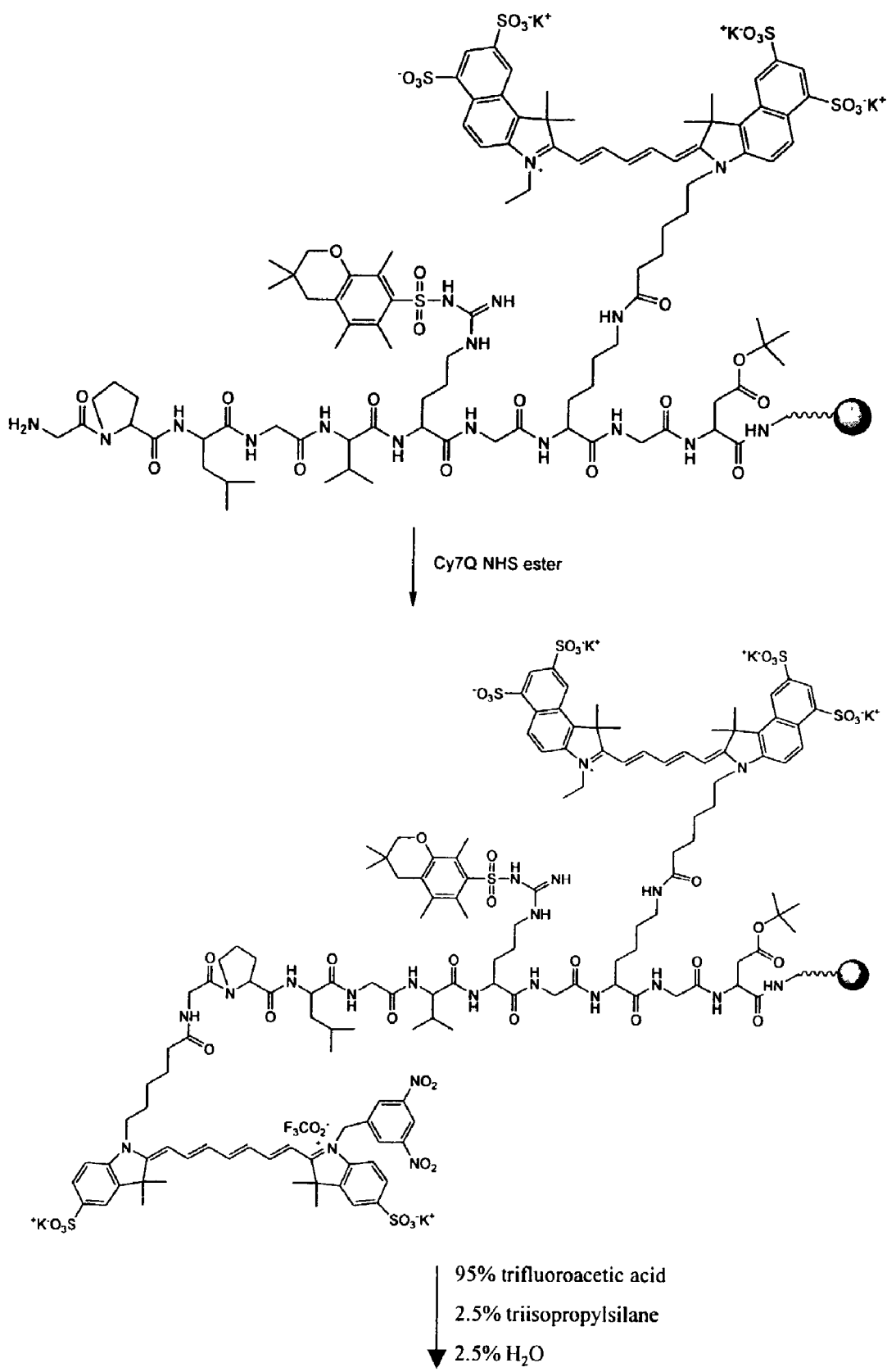
Figure 1C:
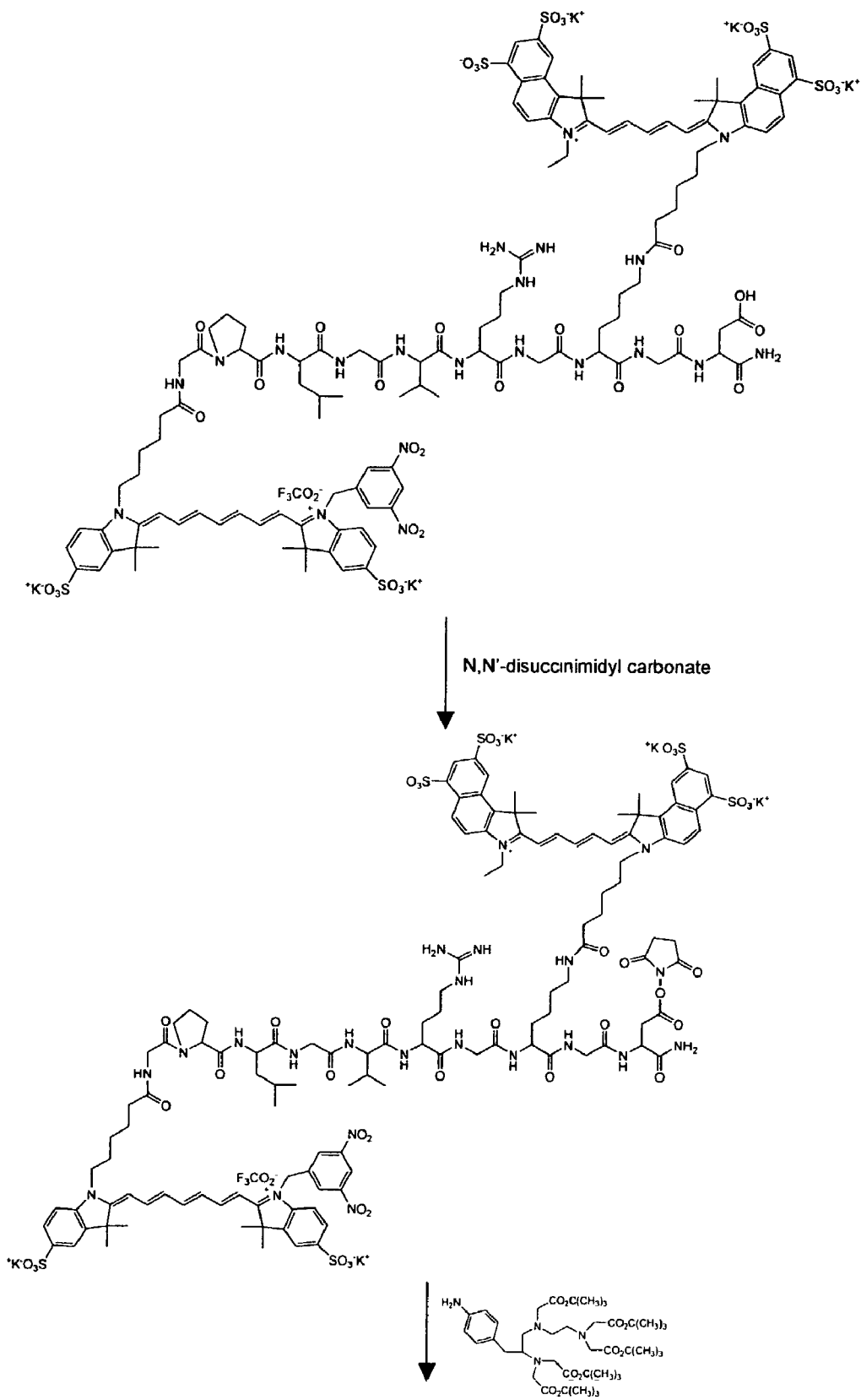
Figure 1D:
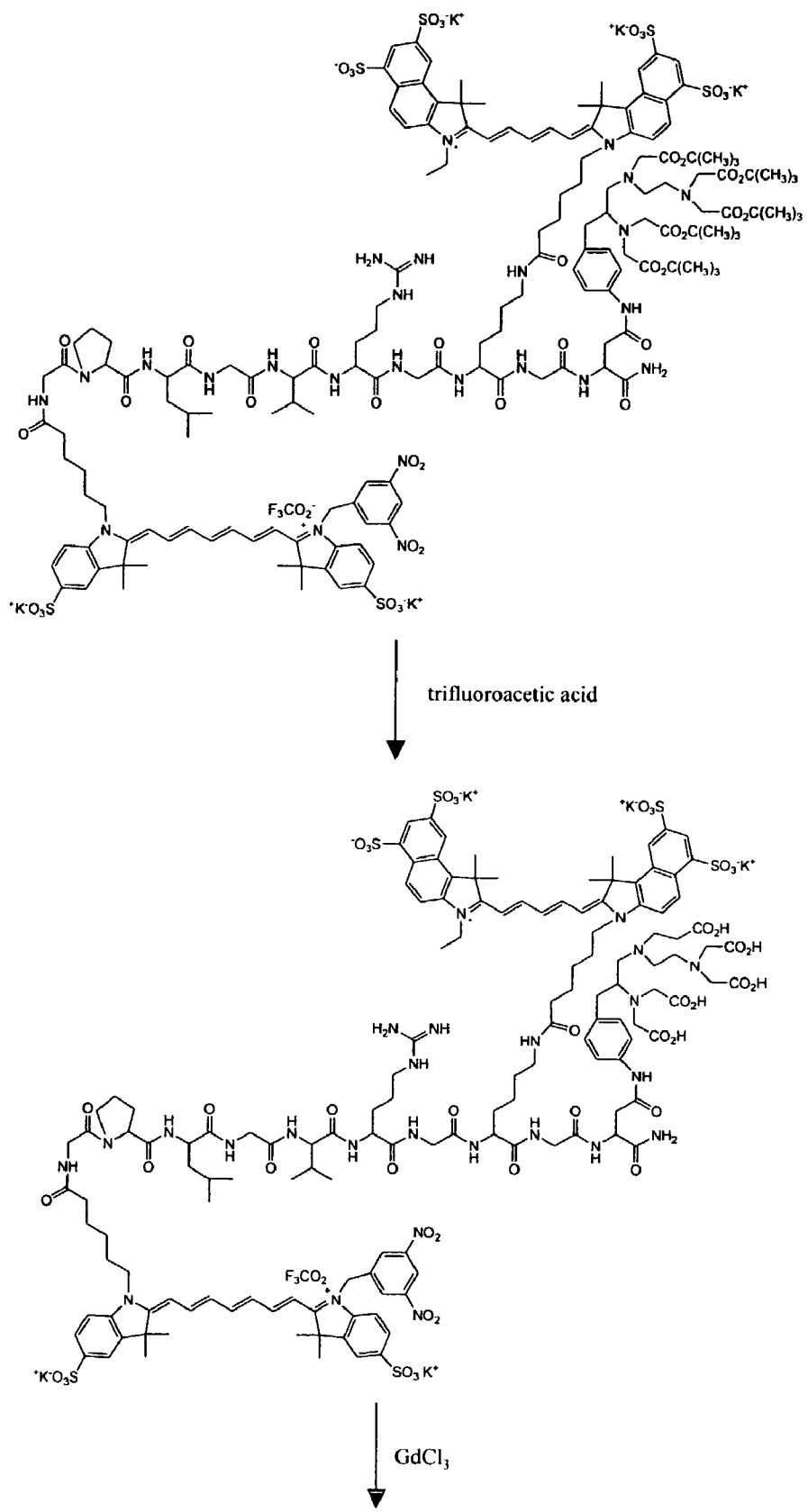

For the purposes of promoting an understanding of the invention, reference will now be made to some preferred embodiments of the present invention as illustrated in FIGS. 1A-3D, and specific language used to describe the same. The terminology used herein is for the purpose of description, not limitation. Specific structural and functional details disclosed herein are not to be interpreted as limiting, but merely as a basis for the claims as a representative basis for teaching one skilled in the art to variously employ the present invention. Any modifications or variations in the depicted detection agents and methods of using the same, and such further applications of the principles of the invention as illustrated herein, as would normally occur to one skilled in the art, are considered to be within the spirit of this invention.

Embodiments of the present invention comprise bifunctional detection agents that function as both MRI contrast agents and optically detectable agents or dyes. These bifunctional detection agents aid in the detection of physiological changes associated with biochemical changes in the tissue, which may indicate tissue abnormality, cardiovascular disease, thrombosis, cancer, etc. As used herein, the term "MRI contrast agent" or "magnetic resonance contrast agent" means a molecule that can be used to enhance an MRI image. MRI contrast agents generally comprise a paramagnetic metal ion bound to a chelator. As used herein, a "paramagnetic metal ion" means a metal ion that is magnetized parallel or antiparallel to a magnetic field to an extent proportional to the field. Generally, paramagnetic metal ions are metal ions having unpaired electrons. Some non-limiting examples of suitable paramagnetic ions include: manganese (Mn), praseodymium (Pr), neodymium (Nd), samarium (Sm), europium (Eu), terbium (Tb), dysprosium (Dy), holmium (Ho), erbium (Er), thulium (Tm), ytterbium (Yb), lutetium (Lu) and gadolinium (Gd). As used herein, "optically detectable agent", "optically detectable dye", "optical contrast agent" and/or "optical dye" mean a photoluminescent compound (i.e., a compound that will emit detectable energy after excitation with light). The optical dye may be fluorescent.

In embodiments, the bifunctional detection agents of the present invention comprise a magnetic resonance component and an optical imaging component. The magnetic resonance component comprises a contrast agent that is preferably always activated or "on" so that the localization of this agent can always be detected. Suitable magnetic resonance contrast agents include, but are not limited to, one or more paramagnetic chelates such as Gd-DTPA, Gd-DOTA, a coated iron nanoparticle, or the like. The optical imaging component comprises an activatable contrast agent or dye that is activated only in the presence of a particular event. When the optical imaging component is activated or turned "on", detectable light is emitted. When the optical imaging component is not activated or is not "on", no significant fraction of the re-emitted light falls onto the optical detector. For example, the optical imaging component may be activated or turned "on" by the presence a certain wavelength of light and (1) the presence of a particular biochemical marker, (2) enzymatic cleavage at fluorescence activation sites, (3) when there is an increase or decrease in the temperature, or (4) when there is an increase or decrease in the pH. Some non-limiting examples of biochemical markers that may activate the optical imaging component of the present invention include matrix metalloproteinases, cysteine and serine proteases, or other biochemical markers that tend to be preferentially over-expressed in pathological conditions. Suitable optical imaging contrast agents include, but are not limited to, compounds comprising the following dyes or modified versions of these dyes: Cy5, Cy5.5, Cy7, IRD41, IRD700, NIR-1, LaJolla Blue, IR780, Indocyanine Green (ICG), Alexa Fluor dyes, or the like.

In one embodiment, the bifunctional detection agents comprise a magnetic resonance contrast agent covalently linked to an optical dye and a quencher molecule. In another embodiment, the bifunctional detection agents comprise a magnetic resonance contrast agent covalently linked to at least two optical dyes. In yet another embodiment, the bifunctional detection agents comprise a magnetic resonance contrast agent covalently linked to multiple optical dyes and multiple quencher molecules.

The dye(s) and/or quencher(s) of the optical imaging component are generally located in close proximity to one another, for example less than 100 Angstroms apart. Additionally, in some embodiments, the dyes used in the optical imaging component emit light slightly shifted towards the red part of the spectrum when excited from outside the body at the proper excitation frequency. Generally, when the optical imaging component is not activated or "on", the dye(s) or the dye(s) and the quencher(s) are in close proximity to one another, causing the emitted light to be reabsorbed and therefore, be undetected by the optical detector. In these embodiments, when the spacing between the dye(s), or the spacing between the dye(s) and the quencher(s), is compromised or increased, the optical imaging component is activated or turned "on", thereby causing light to be emitted that can be detected by the optical detector. The optical imaging component may be designed so that the spacing between the dye(s), or the spacing between the dye(s) and the quencher(s), is compromised or increased only as the result of some biological or signaling process. Some non-limiting examples of such biological or signaling processes include: the presence of certain enzymes or biochemical changes in the body for which the optical imaging component has been precisely designed to detect; a change in the temperature of the tissue; or a change of the local pH of the tissue. The presence of such biological or signaling processes causes bond breakage or conformation change, thereby compromising and increasing the spacing between the dye(s), or the spacing between the dye(s) and the quencher(s), and causing detectable light to be emitted.

The present invention also comprises methods of obtaining high-resolution, in vivo images of biochemical activity in a living organism. One method comprises estimating the localization of the detection agent using one modality (i.e., MRI), while concurrently estimating the level of biological activity using a second modality (i.e., optical imaging). Another method comprises obtaining an image of anatomical information of a living organism and obtaining an image of functional information of the living organism, wherein a bifunctional detection agent is present within the living organism. In this embodiment, the bifunctional detection agent comprises a first component capable of enhancing anatomical information of the living organism and an activatable second component capable of enhancing functional information of the living organism, and the activatable second component is activated only in the presence of a predetermined event. The bifunctional detection agents of the present invention may be administered in any suitable way, preferably via intravenous injection.

The bifunctional detection agents of the present invention allow both anatomical and functional information to be obtained simultaneously via two different modalities. In embodiments of the present invention, a first modality (i.e, magnetic resonance imaging) provides high-resolution anatomical information from which the precise anatomical localization of the detection agent can be determined. In embodiments of the present invention, a second modality (i.e., optical imaging) provides functional or metabolic information. This combination of anatomical and functional information allows for easier and earlier diagnosis and treatment of diseases than currently exits, thereby improving the patient's chance of recovery and/or of being cured.

In an embodiment, the bifunctional detection agents may comprise a polymer or co-polymer selectively grafted and/or end-terminated with optical dye #1, optical dye #2 and the MRI contrast agent. Some non-limiting examples of such agents include:

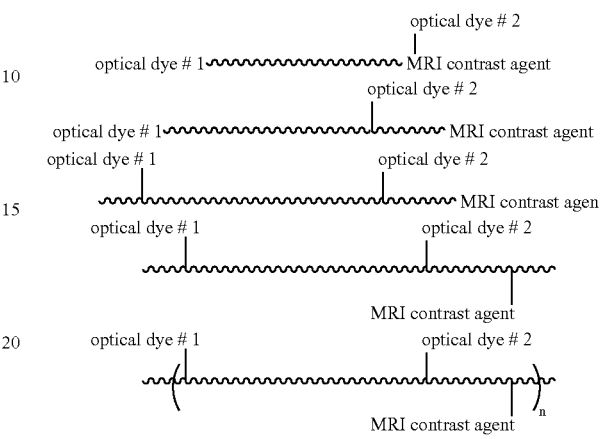

where ∿∿∿ can be a polymer (i.e., polypeptide) or co-polymer (i.e., polypeptide/pNA co-polymer) and — represents moiety covalently linked to the polymer or co-polymer (i.e., amino acid or pNA side chain). The optical dyes comprise commercially available dyes such as, for example, Cy7Q (Dye #1) and Cy5.5 (Dye #2). The MRI contrast agent is covalently linked to the polymer or co-polymer, and is preferably a chelated gadolinium complex such as, for example, Gd-(DTPA). Various alternative optical dyes and magnetic contrast agents may be used without deviating from the scope of this invention, so long as the optical dyes are activatable only in the presence of a predetermined event(s).

In other embodiments, the bifunctional detection agents may comprise:

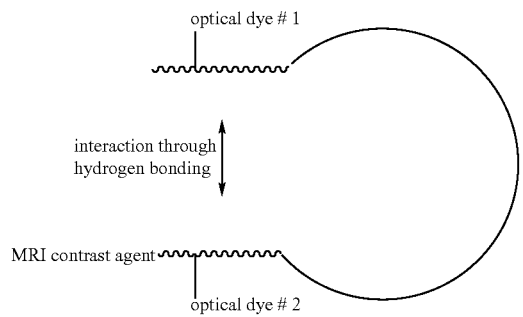

One bifunctional detection agent of the present invention may be synthesized as shown in FIGS. 1A-1E, and as more fully described below. First, a polymer, such as, for example, the polypeptide Fmoc-N-Gly-Pro-Leu-Gly-Val-Arg(Pmc)-Gly-Lys(Aloc)-Gly-Asp(OBut)-C-linker-resin, can be synthesized via solid phase synthesis with standard Fmoc chemistry using various linkers and solid-state supports or resins. Any suitable amino acid sequence may be used in the polymer. Fmoc protected amino acids and solid-state supports can be purchased from commercial suppliers, and the peptide synthesis can be automated with a peptide synthesizer, if desired. The synthesis of the peptide is started at the C terminal end with commercially available polystyrene resin. The carboxylic acid group on the aspartic acid is protected with the acid-sensitive protecting group tertiary butyl ester (OBut). The amine group on the lysine side-chain is protected with the orthogonal protecting group allyloxy-carbonyl (Aloc). The guandinium group on the arginine amino acid is protected with an acid-sensitive protecting group such as 2,2,4,6,7-pentamethyl-dihydrobenzofuran-5-sulfonyl (Pmc) to yield:

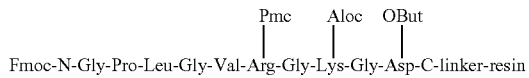

Treatment of the protected 10 mer peptide with a palladium complex such as palladium tetrakis triphenylphosphine (Pd (PPh$_3$)$_4$), acetic acid, and tributyltin hydride removes the Aloc protecting group and leaves a free amine to yield:

The compound is then treated with amine-reactive Cy5.5 NHS ester to yield:

De-protection of the N-terminus with 20% piperidine in DMF removes the Fmoc group and gives a free amine:

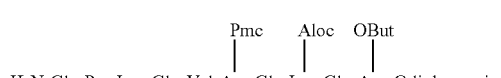

Treating the compound with amine-reactive Cy7Q NHS ester yields:

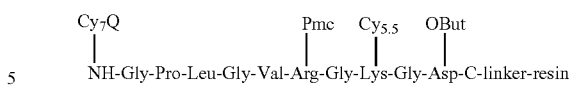

Acid, such as trifluoroacetic acid, in the presence of an appropriate scavenger may then be used to cleave the dye-peptide conjugate from the solid-phase support, while the arginine amino acid and the aspartic acid amino acid are de-protected at the same time to yield:

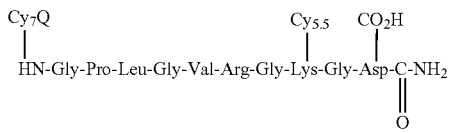

The compound is then treated with the appropriate activating agent, such as disuccinimidyl carbonate, to activate the carboxylic acid and yield:

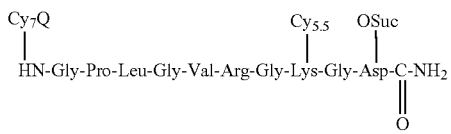

The compound is then treated with p-aminobenzyl-DTPA-penta(t-Bu)ester to yield:

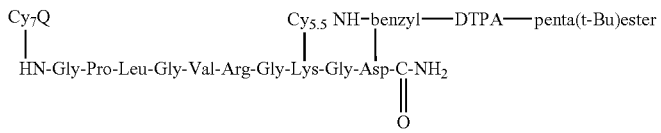

The carboxylic acid groups of the bifunctional ligand are deprotected by treatment with trifluoroacetic acid to remove the t-butyl groups to yield:

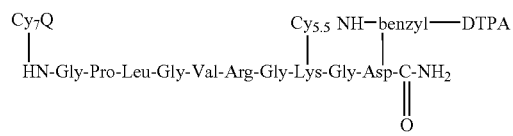

Finally, gadolinium is chelated to the carboxylic acid groups of DTPA by treatment with GdCl$_3$, and the pH is adjusted to give a bifunctional detection agent of the present invention:

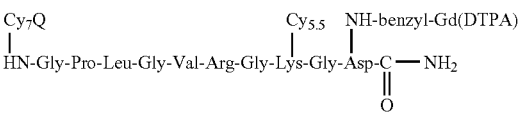

Figure 1E:
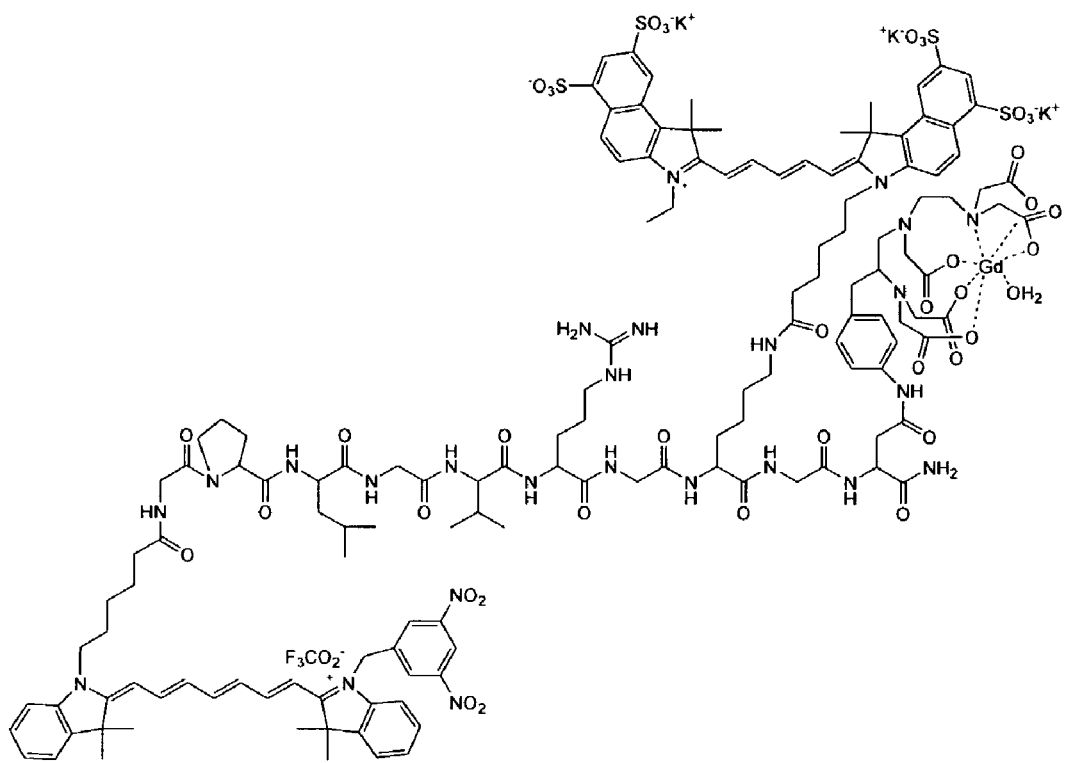

The final chemical structure of this embodiment is shown in FIG. 1E. In this embodiment, Cy5.5 was selected because is has the least interference from heme, deoxy-heme, tissue, water, etc. Cy5.5 absorbs light at about 673 nm, and emits light at about 692 nm. Cy7Q was selected as the "dark" dye because it does not emit light, it only absorbs the light emitted from Cy5.5, as long as the Cy5.5 and Cy7Q are less than about 100 Angstroms apart (i.e., if the string of amino acids remains intact). When the Cy7Q and the Cy5.5 are in close proximity to one another (i.e., within about 100 Angstroms of one another) the Cy7Q acts as a quencher. However, when a predetermined event exists (i.e., a certain enzyme is present), the amino acid chain is cleaved between the amino acid residues, thereby activating the optical imaging component of this compound, and allowing optically detectable light to be emitted. The Gd-(DTPA) was selected as the magnetic resonance contrast agent that is always "on".

Figure 2A:
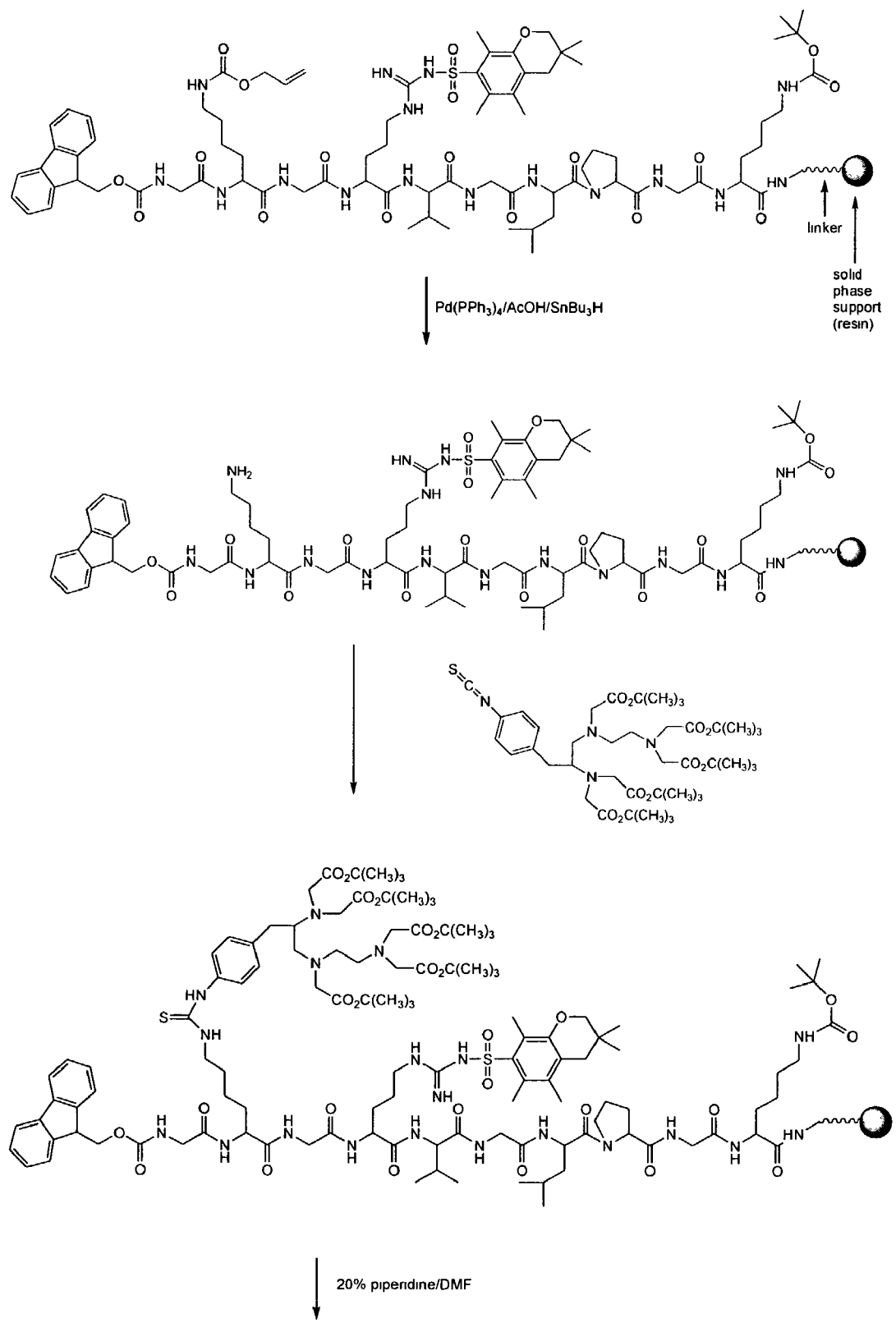
FIGS. 2A-2D show the synthesis of a bifunctional detection agent in accordance with another exemplary embodiment of the present invention.
Figure 2B:
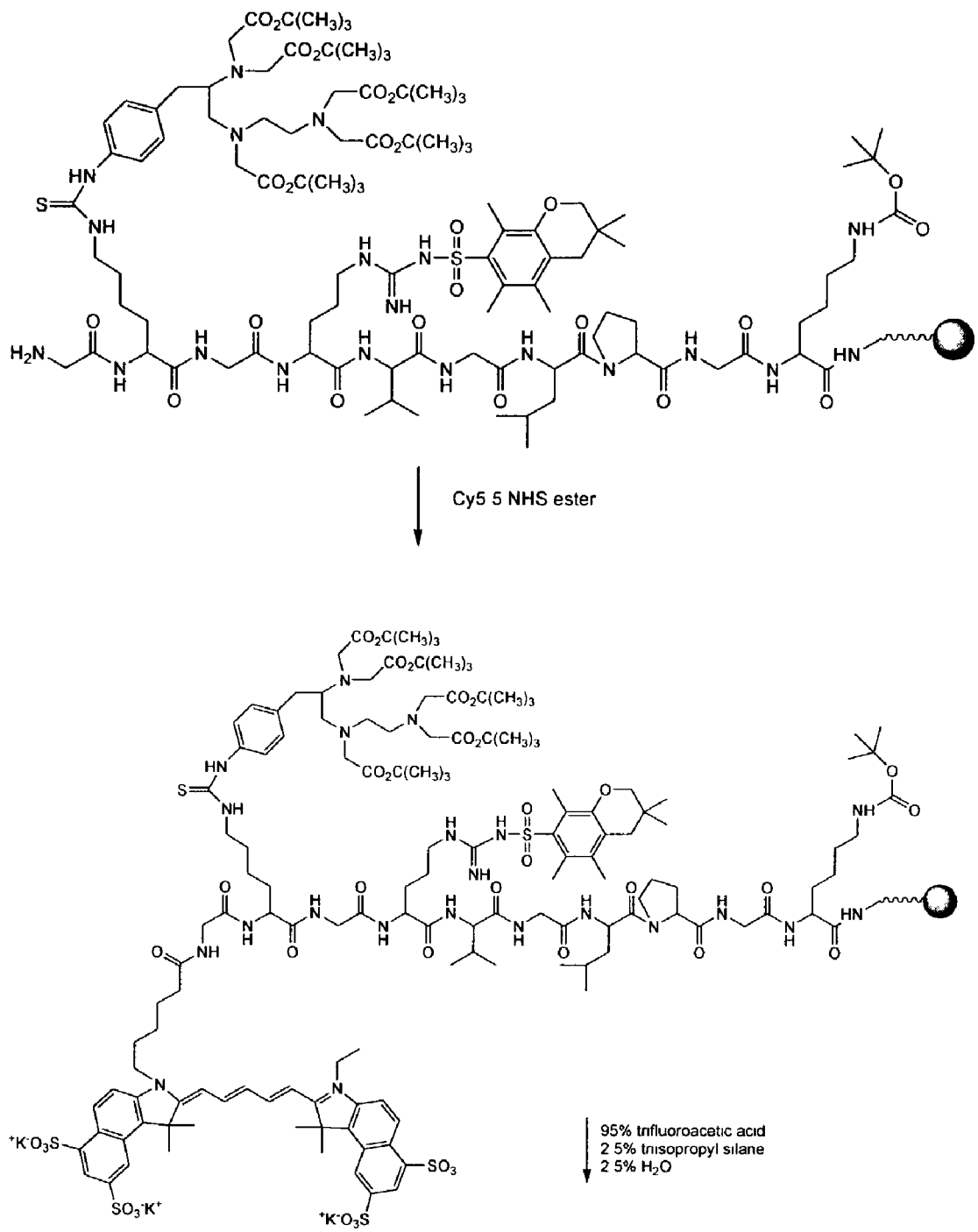
Figure 2C:
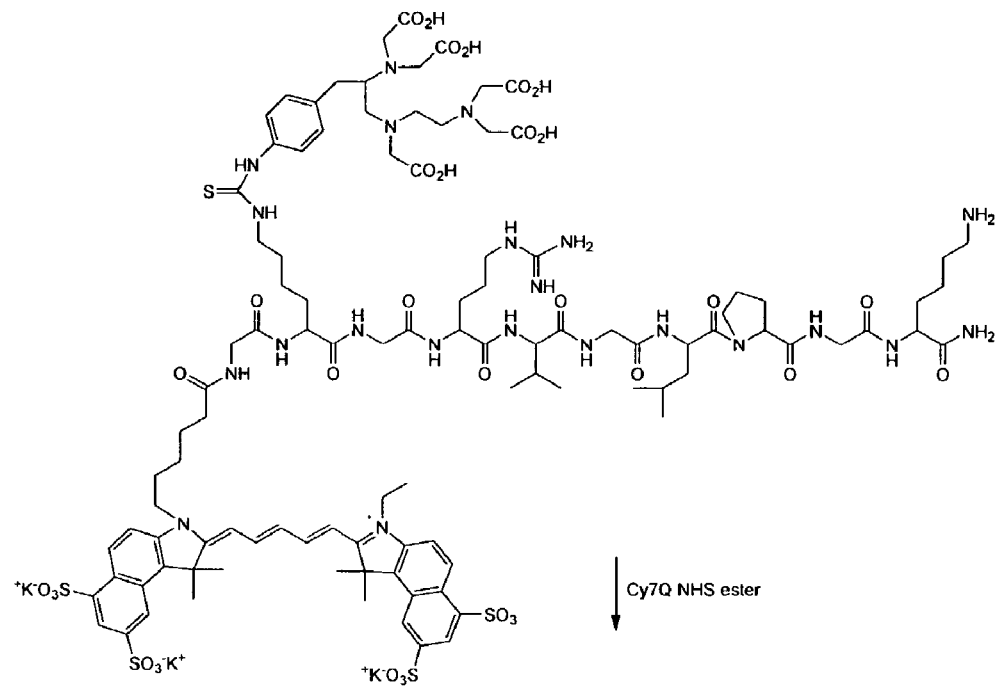
Figure 2C:
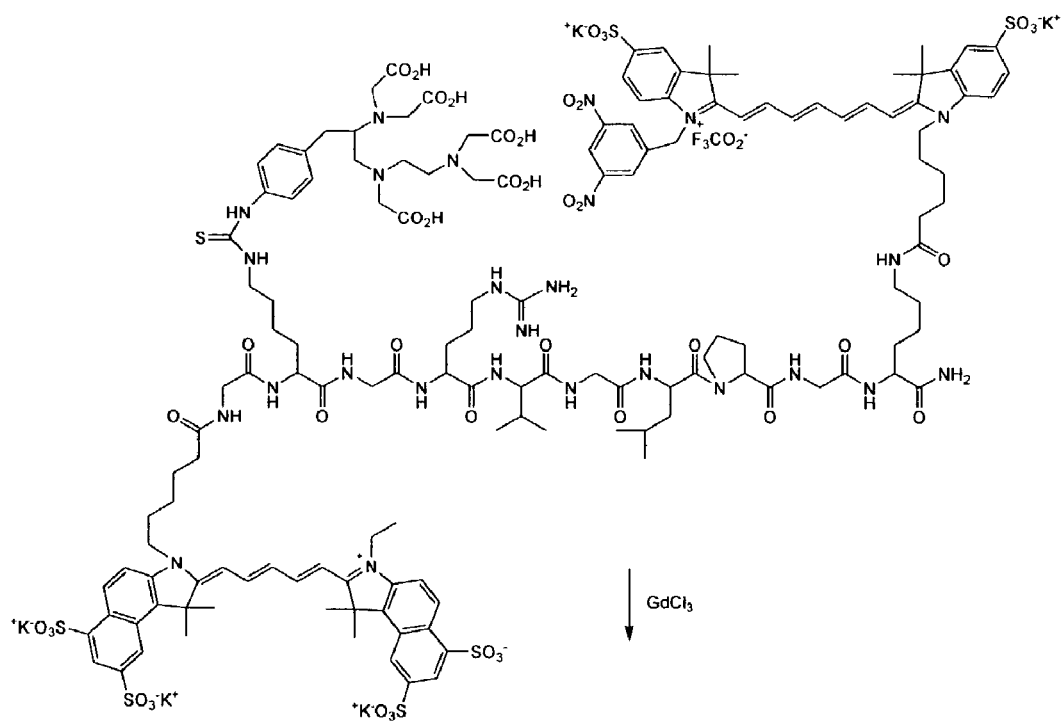
Figure 2D:
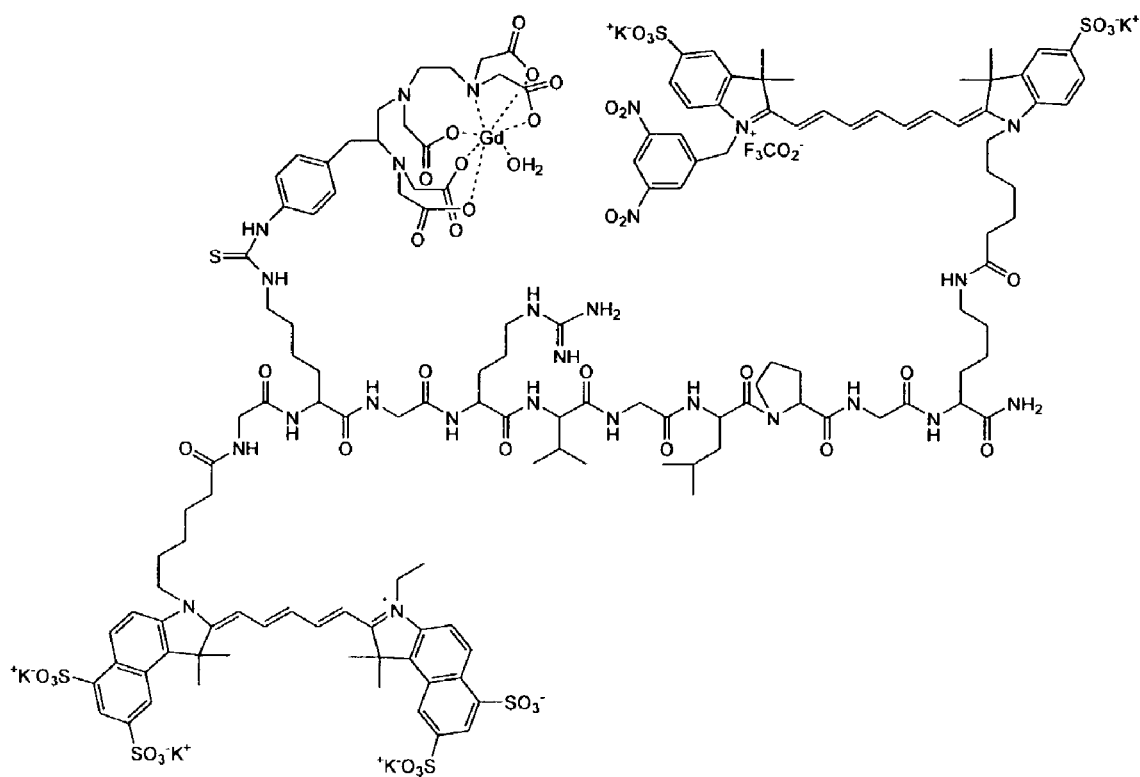

FIGS. 2A-2D show the synthesis of another bifunctional detection agent of the present invention, and the final chemical structure of this particular embodiment is shown in FIG. 2D. This embodiment may be synthesized by methods similar to the methods described for FIGS. 1A-1E.

Figure 3A:
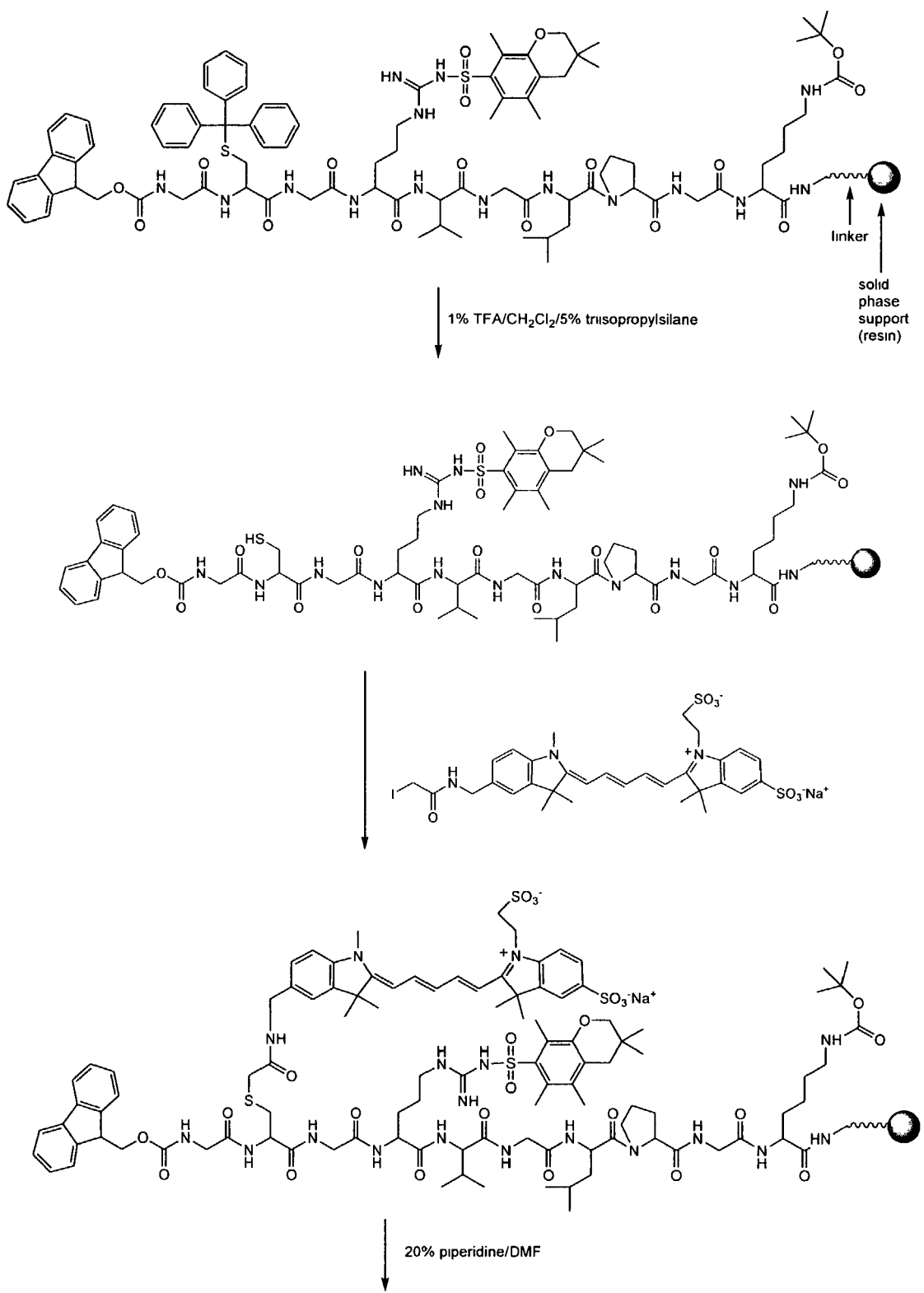
FIGS. 3A-3D show the synthesis of a bifunctional detection agent in accordance with a third exemplary embodiment of the present invention.
Figure 3B:
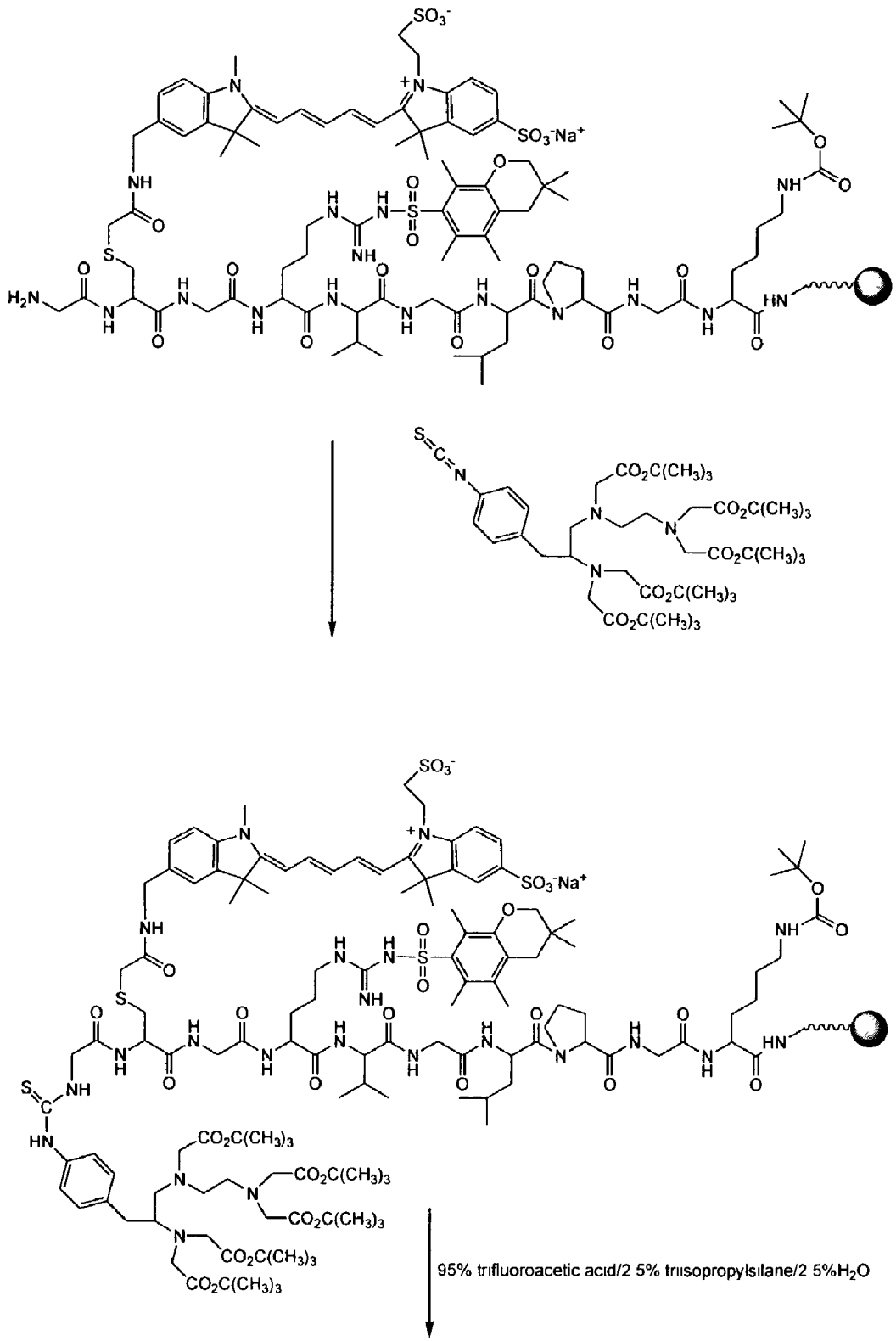
Figure 3C:
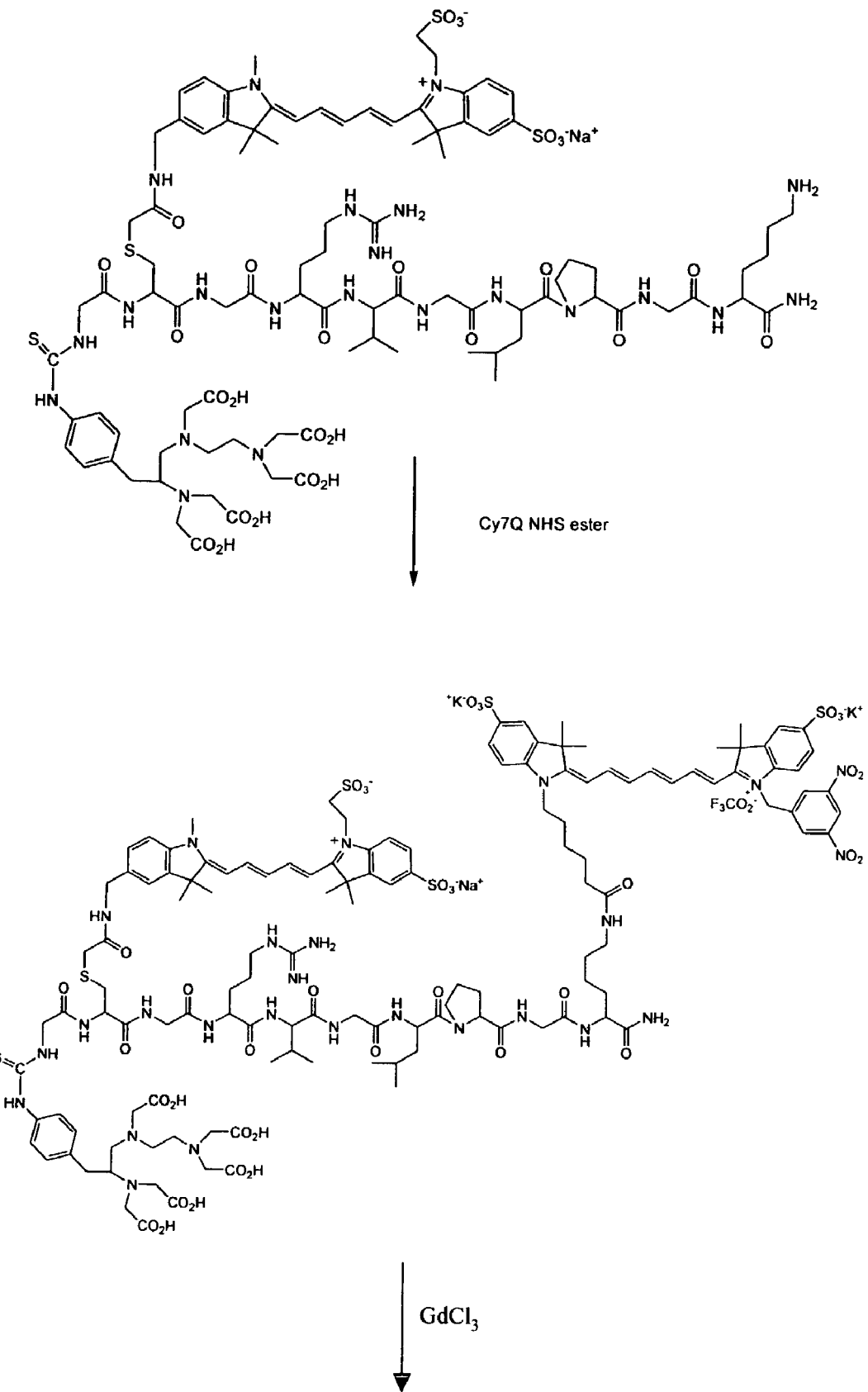
Figure 3D:
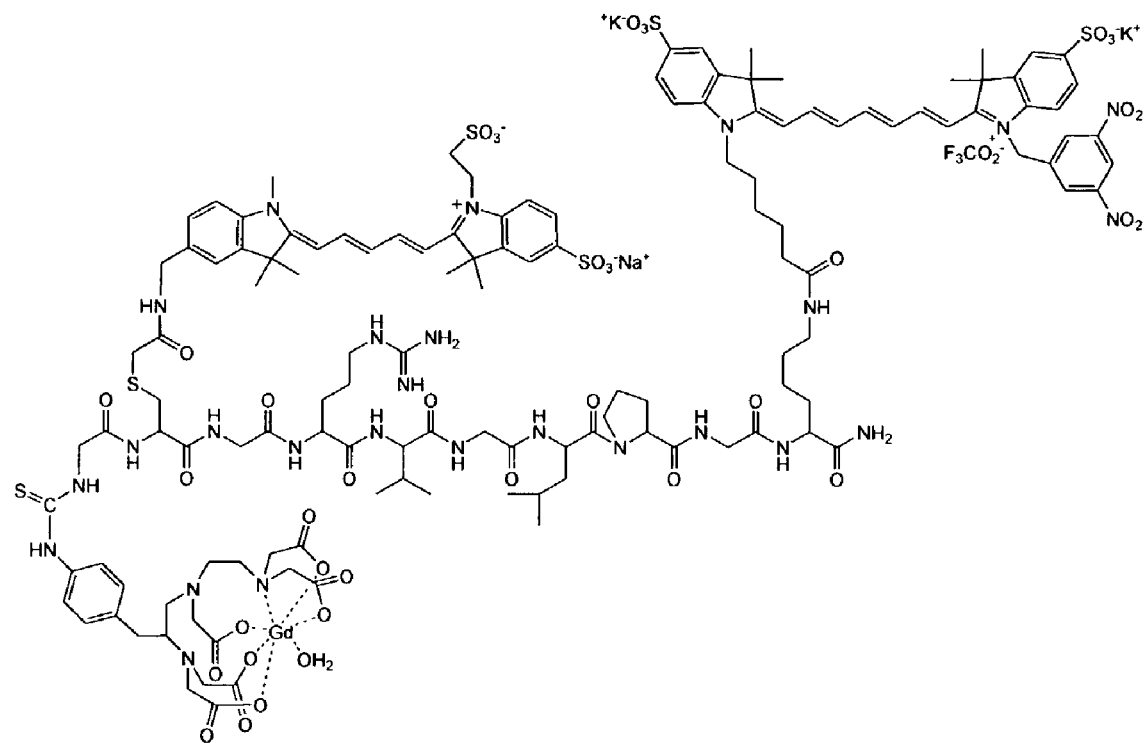

FIGS. 3A-3D show the synthesis of yet another bifunctional detection agent of the present invention, and the final chemical structure of this particular embodiment is shown in FIG. 3D. This embodiment may also be synthesized by methods similar to the methods described for FIGS. 1A-1E.

While bifunctional detection agents for concurrent use in combination MRI/optical imaging systems have been described above, it is understood that bifunctional detection agents may be designed for concurrent use in alternative combination imaging systems without deviating from the scope of the present invention. For example, a bifunctional detection agent for concurrent use in computed tomography (CT) and optical imaging, or for concurrent use in positron emission tomography (PET) and optical imaging, also falls within the scope of this invention so long as the CT/PET contrast agent is always "on" or activated and the optical imaging component is activatable only in the presence of a specific predetermined event. Other diagnostic imaging techniques that may be combined with optical imaging include: X-ray based techniques, ultrasound, diagnostic techniques based on radioactive materials (e.g. scintigraphy and SPECT), and the like.

Various embodiments of the invention have been described above. However, it should be recognized that these embodiments are merely illustrative of the principles of various embodiments of the present invention. Numerous modifications and adaptations thereof will be apparent to those skilled in the art without departing from the spirit and scope of the present invention. Thus, it is intended that the present invention cover all suitable modifications and variations as come within the scope of the appended claims and their equivalents.

What is claimed is:

1. A bifunctional detection agent comprising:

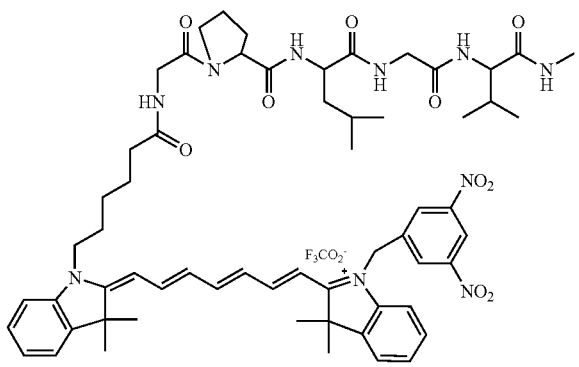

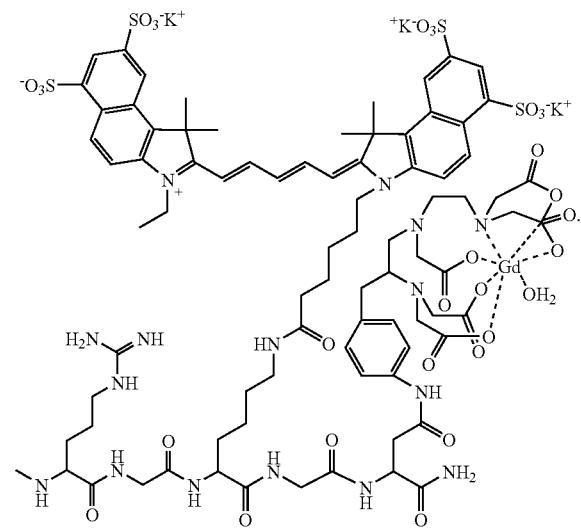

2. A bifunctional detection agent comprising:
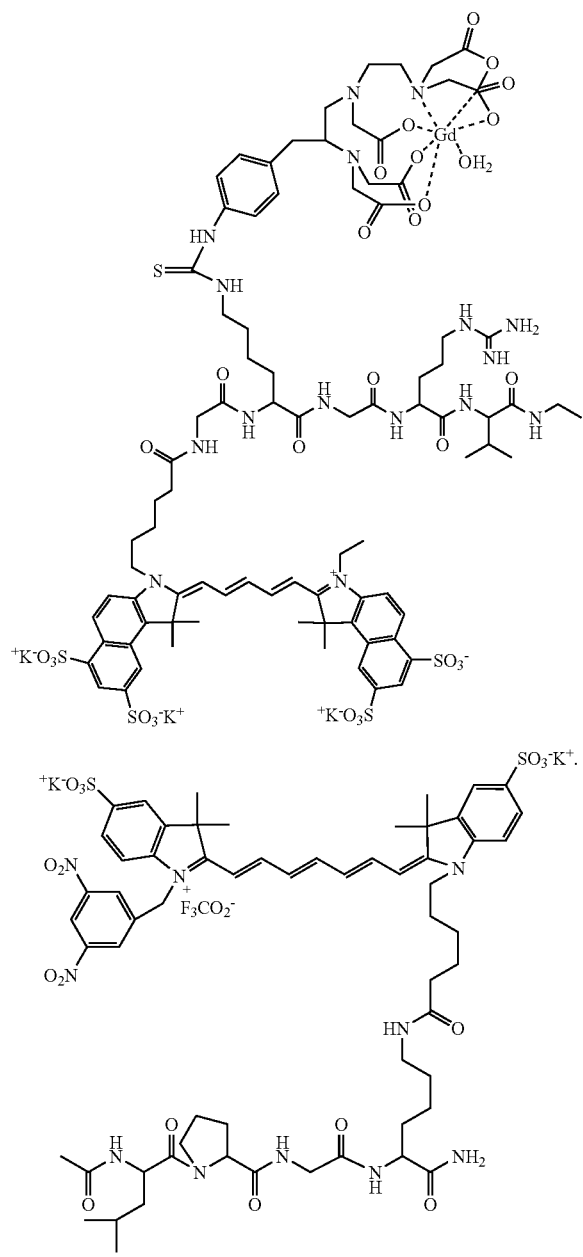
3. A bifunctional detection agent comprising:
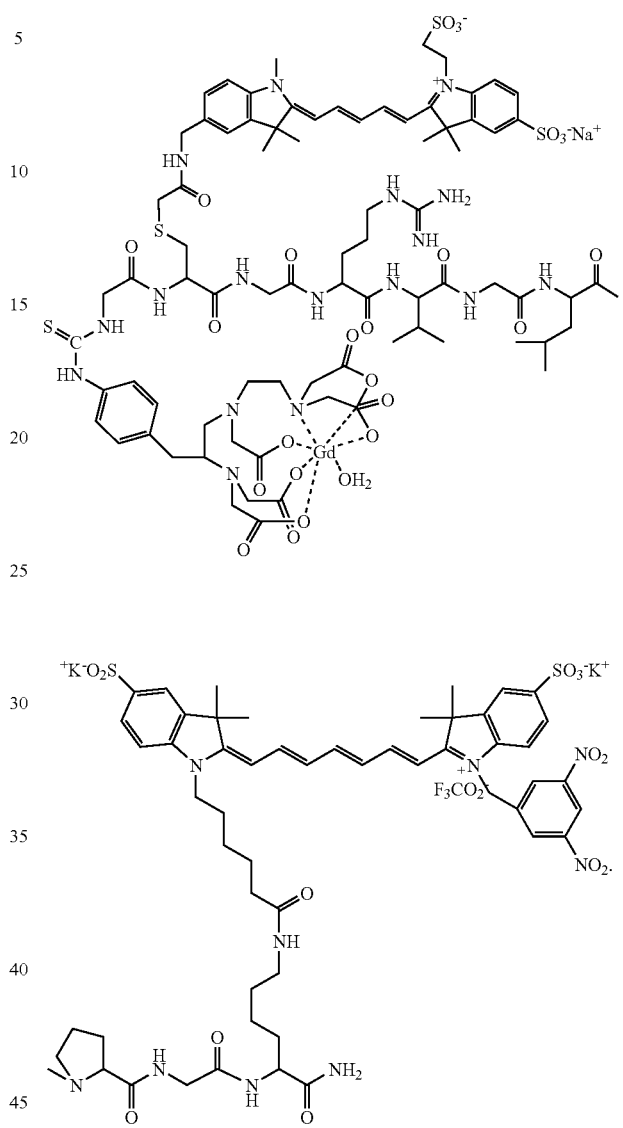
* * * * *

UNITED STATES PATENT AND TRADEMARK OFFICE
CERTIFICATE OF CORRECTION

PATENT NO.      : 7,303,741 B2
APPLICATION NO. : 10/252311
DATED           : December 4, 2007
INVENTOR(S)     : Hancu et al.

It is certified that error appears in the above-identified patent and that said Letters Patent is hereby corrected as shown below:

In Fig. 1A, Sheet 1 of 13, delete "↓ Cy5 5 NHS ester" and insert -- ↓ Cy5.5 NHS ester --, therefor.

In Fig. 2B, Sheet 7 of 13, delete "↓ Cy5 5 NHS ester" and insert -- ↓ Cy5.5 NHS ester --, therefor.

In Fig. 2B, Sheet 7 of 13, delete "↓ 95% trifluoroacetic acid / 2.5% triisopropyl silane / 2.5% H₂O" and insert -- ↓ 95% trifluoroacetic acid / 2.5% triisopropylsilane / 2.5% H₂O --, therefor.

In Fig. 3B, Sheet 11 of 13, delete "↓ 95% trifluoroacetic acid/2.5% triisopropylsilane/2.5%H₂O" and insert -- ↓ 95% trifluoroacetic acid/2.5% triisopropylsilane/2.5%H₂O --, therefor.

UNITED STATES PATENT AND TRADEMARK OFFICE
CERTIFICATE OF CORRECTION

PATENT NO. : 7,303,741 B2
APPLICATION NO. : 10/252311
DATED : December 4, 2007
INVENTOR(S) : Hancu et al.

It is certified that error appears in the above-identified patent and that said Letters Patent is hereby corrected as shown below:

In Column 2, Line 50, delete "feruimoxsil" and insert -- ferumoxsil --, therefor.

In Column 8, Line 12, delete "tern" and insert -- term --, therefor.

In Column 10, Line 15, delete "agen" and insert -- agent --, therefor.

In Column 11, Line 46, delete "$Cy_{5.5}$" and insert -- Cy5.5 --, therefor at each occurrence in Columns 11-12.

In claim 1, the formula appears in two parts. Please replace the formula of claim 1 with the following formula:

1. A bifunctional detection agent comprising:

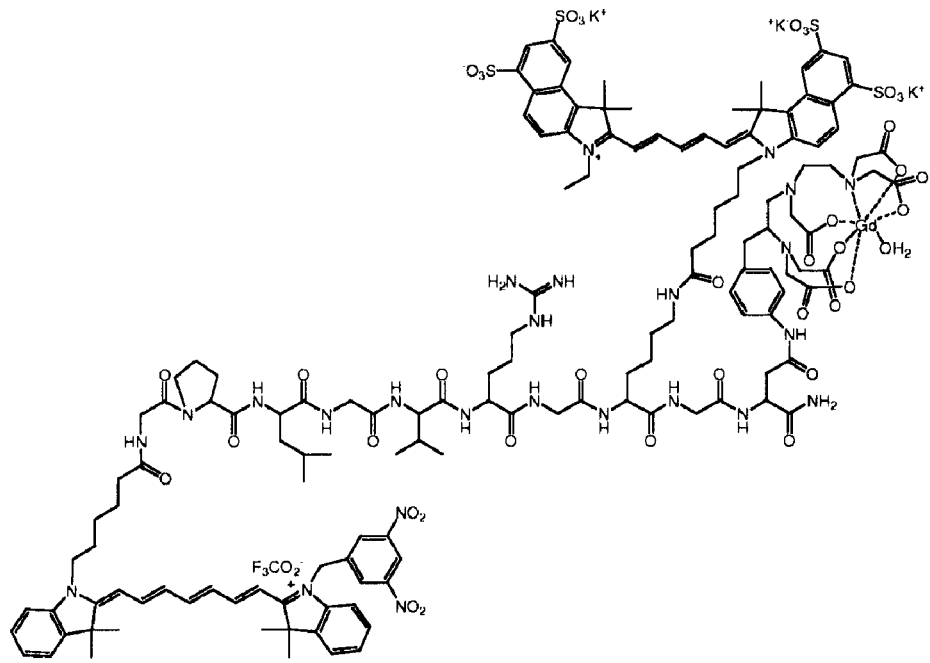

UNITED STATES PATENT AND TRADEMARK OFFICE
CERTIFICATE OF CORRECTION

PATENT NO. : 7,303,741 B2 Page 3 of 4
APPLICATION NO. : 10/252311
DATED : December 4, 2007
INVENTOR(S) : Hancu et al.

It is certified that error appears in the above-identified patent and that said Letters Patent is hereby corrected as shown below:

In claim 2, the formula appears in two parts. Please replace the formula of claim 2 with the following formula:

2. A bifunctional detection agent comprising:

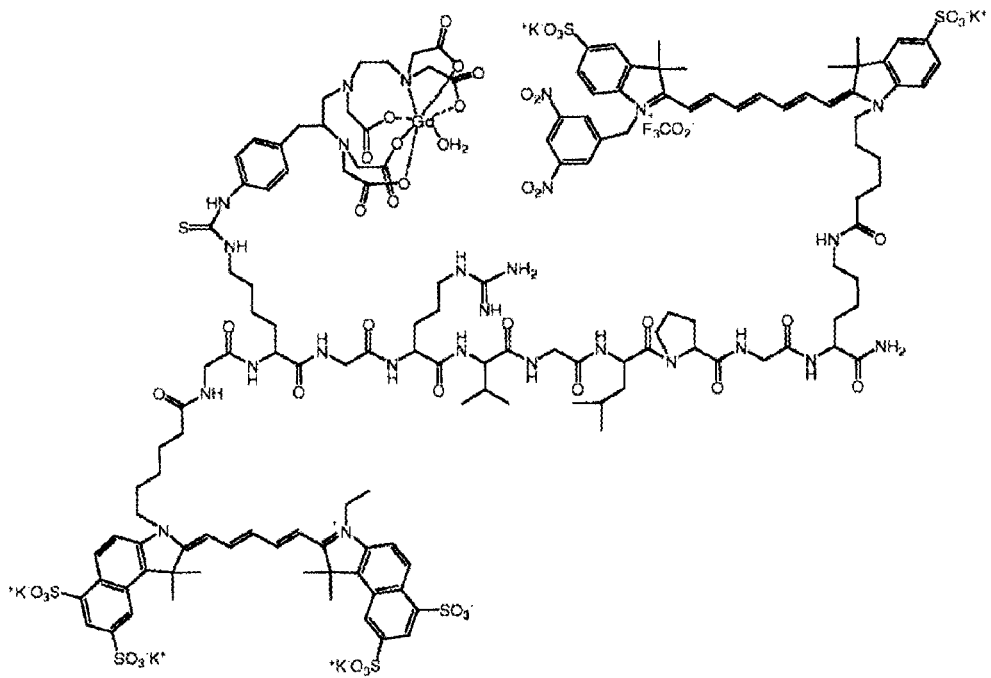

UNITED STATES PATENT AND TRADEMARK OFFICE
CERTIFICATE OF CORRECTION

PATENT NO. : 7,303,741 B2
APPLICATION NO. : 10/252311
DATED : December 4, 2007
INVENTOR(S) : Hancu et al.

It is certified that error appears in the above-identified patent and that said Letters Patent is hereby corrected as shown below:

In claim 3, the formula appears in two parts. Please replace the formula of claim 3 with the following formula:

3. A bifunctional detection agent comprising:

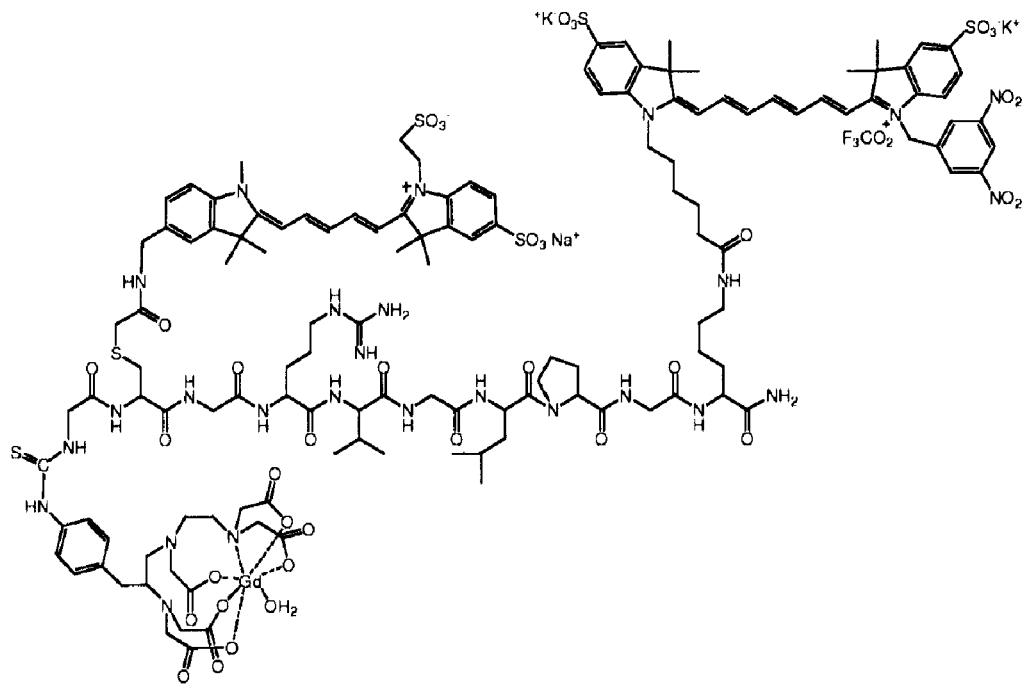

Signed and Sealed this

Second Day of September, 2008

JON W. DUDAS
*Director of the United States Patent and Trademark Office*

UNITED STATES PATENT AND TRADEMARK OFFICE
CERTIFICATE OF CORRECTION

PATENT NO. : 7,303,741 B2  
APPLICATION NO. : 10/252311  
DATED : December 4, 2007  
INVENTOR(S) : Hancu et al.

It is certified that error appears in the above-identified patent and that said Letters Patent is hereby corrected as shown below:

In Fig. 1A, Sheet 1 of 13, delete "↓ Cy5 5 NHS ester" and insert -- ↓ Cy5.5 NHS ester --, therefor.

In Fig. 2B, Sheet 7 of 13, delete "↓ Cy5 5 NHS ester" and insert -- ↓ Cy5.5 NHS ester --, therefor.

In Fig. 2B, Sheet 7 of 13, delete "↓ 95% trifluoroacetic acid / 2.5% triisopropyl silane / 2.5% H₂O" and insert -- ↓ 95% trifluoroacetic acid / 2.5% triisopropylsilane / 2.5% H₂O --, therefor.

In Fig. 3B, Sheet 11 of 13, delete "↓ 95% trifluoroacetic acid/2.5% triisopropylsilane/2.5%H₂O" and insert -- ↓ 95% trifluoroacetic acid/2.5% triisopropylsilane/2.5%H₂O --, therefor.

UNITED STATES PATENT AND TRADEMARK OFFICE
CERTIFICATE OF CORRECTION

PATENT NO. : 7,303,741 B2
APPLICATION NO. : 10/252311
DATED : December 4, 2007
INVENTOR(S) : Hancu et al.

It is certified that error appears in the above-identified patent and that said Letters Patent is hereby corrected as shown below:

In Column 2, Line 50, delete "feruimoxsil" and insert -- ferumoxsil --, therefor.

In Column 8, Line 12, delete "tern" and insert -- term --, therefor.

In Column 10, Line 15, delete "agen" and insert -- agent --, therefor.

In Column 11, Line 46, delete "$Cy_{5.5}$" and insert -- Cy5.5 --, therefor at each occurrence in Columns 11-12.

Column 14, In claim 1, the formula appears in two parts. Please replace the formula of claim 1 with the following formula:

1. A bifunctional detection agent comprising:

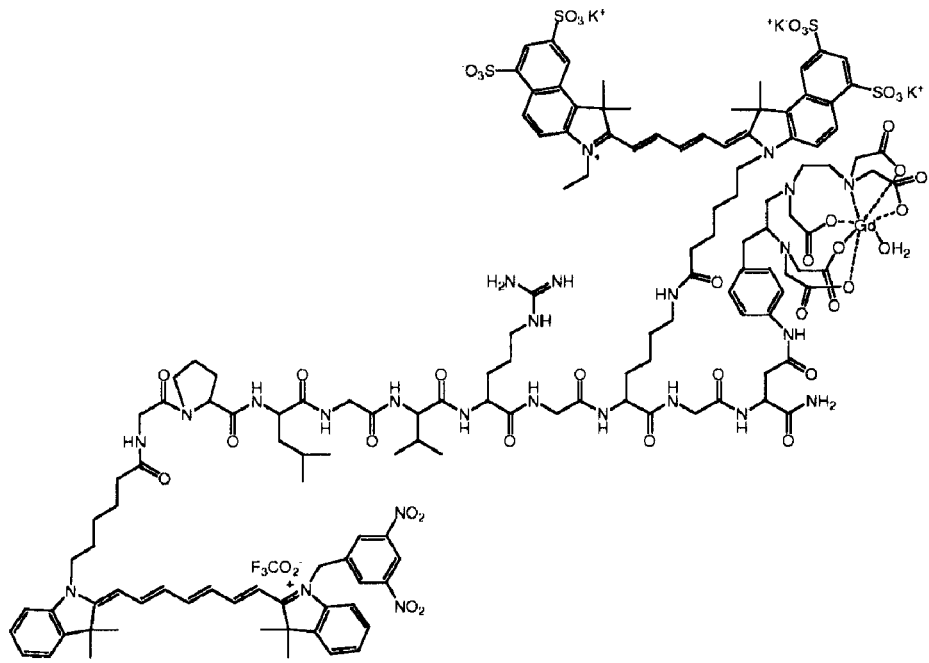

UNITED STATES PATENT AND TRADEMARK OFFICE
CERTIFICATE OF CORRECTION

PATENT NO.       : 7,303,741 B2
APPLICATION NO.  : 10/252311
DATED            : December 4, 2007
INVENTOR(S)      : Hancu et al.

Page 3 of 4

It is certified that error appears in the above-identified patent and that said Letters Patent is hereby corrected as shown below:

Column 15, In claim 2, the formula appears in two parts. Please replace the formula of claim 2 with the following formula:

2. A bifunctional detection agent comprising:

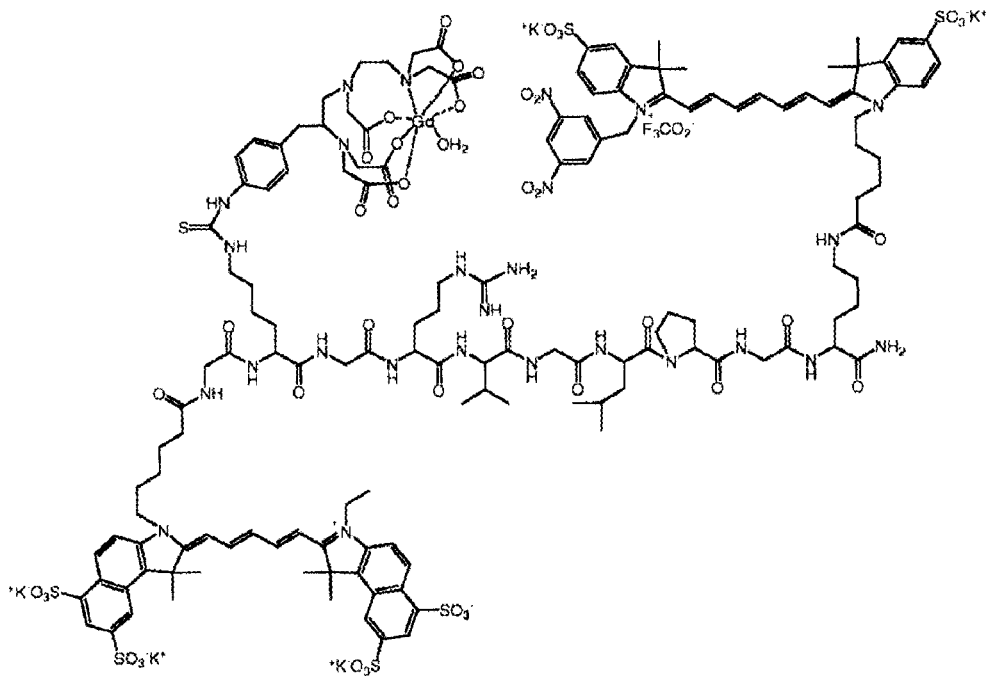

Column 16, In claim 3, the formula appears in two parts. Please replace the formula of claim 3 with the following formula:

UNITED STATES PATENT AND TRADEMARK OFFICE
CERTIFICATE OF CORRECTION

PATENT NO. : 7,303,741 B2  Page 4 of 4
APPLICATION NO. : 10/252311
DATED : December 4, 2007
INVENTOR(S) : Hancu et al.

It is certified that error appears in the above-identified patent and that said Letters Patent is hereby corrected as shown below:

3. A bifunctional detection agent comprising:

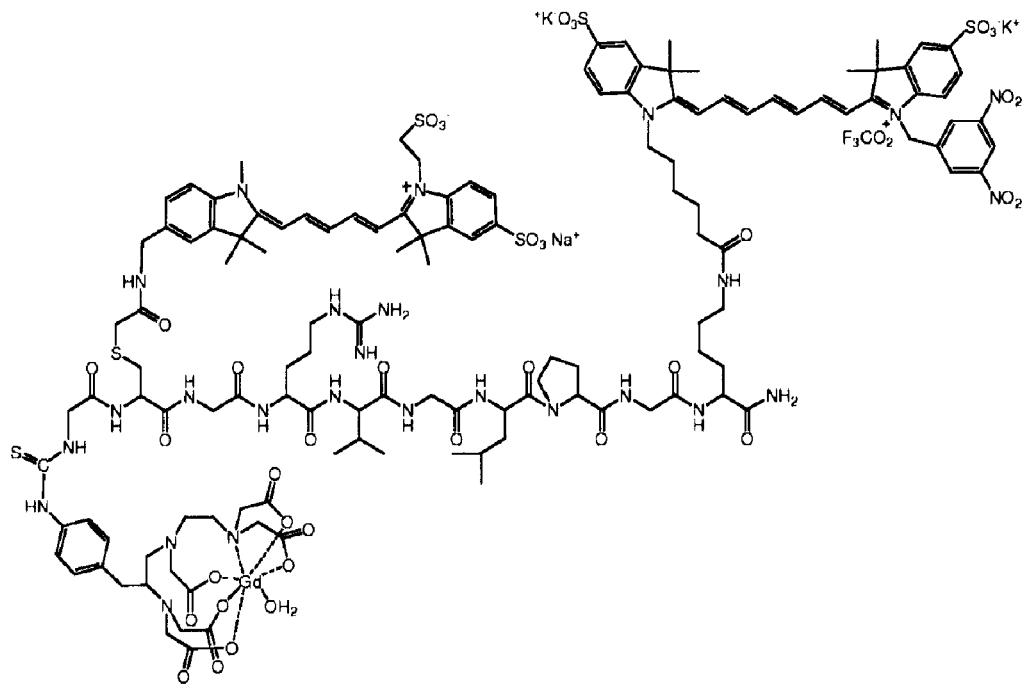

This certificate supersedes the Certificate of Correction issued September 2, 2008.

Signed and Sealed this

Seventh Day of October, 2008

JON W. DUDAS
*Director of the United States Patent and Trademark Office*